(12) United States Patent
Little, II et al.

(10) Patent No.: US 6,376,211 B1
(45) Date of Patent: Apr. 23, 2002

(54) AGENTS AND METHODS FOR INHIBITING $F_1/F_0$ ATPASE

(75) Inventors: Roger G. Little, II, Benicia; Susan Abrahamson, Berkeley, both of CA (US)

(73) Assignee: XOMA Technology Ltd., Berkeley, CA (US)

( * ) Notice: Subject to any disclaimer, the term of this patent is extended or adjusted under 35 U.S.C. 154(b) by 0 days.

(21) Appl. No.: 09/545,112

(22) Filed: Apr. 6, 2000

Related U.S. Application Data
(60) Provisional application No. 60/143,373, filed on Jul. 12, 1999.

(51) Int. Cl.[7] .............................. C12Q 1/42; C12Q 1/00; C12Q 1/18; C12N 9/00
(52) U.S. Cl. .............................. 435/21; 435/31; 435/32; 435/4; 435/183; 530/300
(58) Field of Search ................................. 435/21, 32, 4, 435/31, 183; 530/300

(56) References Cited

U.S. PATENT DOCUMENTS 5,786,150 A * 7/1998 Hillman et al. ................. 435/6
5,948,625 A * 9/1999 Hillman et al. ................. 435/6

OTHER PUBLICATIONS

Abrahams, J. P. et al., "The structure of bovine F–1–ATPase complexed with the peptide antibiotic efrapeptin," *Proceedings of the National Acad. of Sciences of the U.S.*, 93(18):9420–9424 (1996).
Abrahams, J. P. et al., *Biological Abstracts*, abstract No. PREV199699198333, , Philadelphia, PA, US (1996) (Abstract).
Matsuno–Yagi, A. et al., "Studies on the Mechanism of Oxidative Phosphorylation Effects of Specific F–0 Modifiers on Ligand–Induced Conformation Changes of F–1," *Proceedings of the National Acad. of Sciences of the U.S.*, 82(22) 7550–7554 (1985).
Matsuno–Yagi, A. et al., *Biological Abstracts*, vol. 81, abstract No. 49500, Philadelphia, PA, US (1986) (Abstract).
Murray, M. et al., "Antimicrobial testing using oxygen consumption as the indicator of susceptibility," *Archives of Pathology and Laboratory Medicine*, 115(12)1235–1240 (1991).
Murray, M. et al., *Chemical Abstracts*, vol. 117, No. 11, abstract No. 107719, Columbus, Ohio, US (Sep. 14, 1992) (Abstract).
Georgopapadakou, N. H., et al. "Antifungal Agents: Chemotherapeutic Targets and Immunologic Strategies," *Antimicrobial Agents and Chemotherapy*, 40 (2):279–291 (1996).
Monk, B. C. et al., "Fungal Plasma Membrane Proton Pumps as Promising New Antifungal Targets," *Critical Reviews in Microbiology*, 20(3):209–223 (1994).
Portillo, F., et al., "Mode of Action of Miconazole on Yeasts: Inhibition of the Mitochondrial ATPase," *European Journal of Biochemistry*, 143 (2):273–276 (1984).
Odds, F. C. "Antifungal Agents and Their Use in *Candida* Infections," In: Candida and Candidosis, Chapter 27, pp. 279–313 (1979).

* cited by examiner

*Primary Examiner*—Louise N. Leary
(74) *Attorney, Agent, or Firm*—Marshall, Gerstein & Borun.

(57) ABSTRACT

Novel methods of identifying antimicrobial and antiproliferative agents and therapeutic uses are provided.

22 Claims, 1 Drawing Sheet

SEQUENCE LISTING

```
<160> NUMBER OF SEQ ID NOS: 6

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
```

```
<220> FEATURE:
<221> NAME/KEY: mat_peptide
<222> LOCATION: (124)..(1491)

<400> SEQUENCE: 1 cag gcc ttga ggt ttt ggca gct ctg gagg atg aga gag aac atg gcc agg ggc      54
                                        Met Arg Glu Asn Met Ala Arg Gly
                                            -30                 -25 cct tgc aac gcg ccg aga tgg gtg tcc ctg atg gtg ctc gtc gcc ata            102
Pro Cys Asn Ala Pro Arg Trp Val Ser Leu Met Val Leu Val Ala Ile
            -20                 -15                 -10 ggc acc gcc gtg aca gcg gcc gtc aac cct ggc gtg gtg gtc agg atc            150
Gly Thr Ala Val Thr Ala Ala Val Asn Pro Gly Val Val Val Arg Ile
         -5                  -1  1               5 tcc cag aag ggc ctg gac tac gcc agc cag cag ggg acg gcc gct ctg            198
Ser Gln Lys Gly Leu Asp Tyr Ala Ser Gln Gln Gly Thr Ala Ala Leu
 10              15                  20                  25 cag aag gag ctg aag agg atc aag att cct gac tac tca gac agc ttt            246
Gln Lys Glu Leu Lys Arg Ile Lys Ile Pro Asp Tyr Ser Asp Ser Phe
                 30                  35                  40 aag atc aag cat ctt ggg aag ggg cat tat agc ttc tac agc atg gac            294
Lys Ile Lys His Leu Gly Lys Gly His Tyr Ser Phe Tyr Ser Met Asp
             45                  50                  55 atc cgt gaa ttc cag ctt ccc agt tcc cag ata agc atg gtg ccc aat            342
Ile Arg Glu Phe Gln Leu Pro Ser Ser Gln Ile Ser Met Val Pro Asn
         60                  65                  70 gtg ggc ctt aag ttc tcc atc agc aac gcc aat atc aag atc agc ggg            390
Val Gly Leu Lys Phe Ser Ile Ser Asn Ala Asn Ile Lys Ile Ser Gly
     75                  80                  85 aaa tgg aag gca caa aag aga ttc tta aaa atg agc ggc aat ttt gac            438
Lys Trp Lys Ala Gln Lys Arg Phe Leu Lys Met Ser Gly Asn Phe Asp
 90                  95                 100                 105 ctg agc ata gaa ggc atg tcc att tcg gct gat ctg aag ctg ggc agt            486
Leu Ser Ile Glu Gly Met Ser Ile Ser Ala Asp Leu Lys Leu Gly Ser
                 110                 115                 120 aac ccc acg tca ggc aag ccc acc atc acc tgc tcc agc tgc agc agc            534
Asn Pro Thr Ser Gly Lys Pro Thr Ile Thr Cys Ser Ser Cys Ser Ser
             125                 130                 135 cac atc aac agt gtc cac gtg cac atc tca aag agc aaa gtc ggg tgg            582
His Ile Asn Ser Val His Val His Ile Ser Lys Ser Lys Val Gly Trp
         140                 145                 150 ctg atc caa ctc ttc cac aaa aaa att gag tct gcg ctt cga aac aag            630
Leu Ile Gln Leu Phe His Lys Lys Ile Glu Ser Ala Leu Arg Asn Lys
     155                 160                 165 atg aac agc cag gtc tgc gag aaa gta acc aat tct gta tcc tcc aag            678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct            726
Leu Gln Pro Tyr Phe Gln Thr Leu Pro Val Met Thr Lys Ile Asp Ser
                 190                 195                 200 gtg gct gga atc aac tat ggt ctg gtg gca cct cca gca acc acg gct            774
Val Ala Gly Ile Asn Tyr Gly Leu Val Ala Pro Pro Ala Thr Thr Ala
             205                 210                 215 gag acc ctg gat gta cag atg aag ggg gag ttt tac agt gag aac cac            822
Glu Thr Leu Asp Val Gln Met Lys Gly Glu Phe Tyr Ser Glu Asn His
         220                 225                 230 cac aat cca cct ccc ttt gct cca cca gtg atg gag ttt ccc gct gcc            870
His Asn Pro Pro Pro Phe Ala Pro Pro Val Met Glu Phe Pro Ala Ala
     235                 240                 245 cat gac cgc atg gta tac ctg ggc ctc tca gac tac ttc ttc aac aca            918
```

```
                                                                                      -continued His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga          966
Ala Gly Leu Val Tyr Gln Glu Ala Gly Val Leu Lys Met Thr Leu Arg
                    270                 275                 280 gat gac atg att cca aag gag tcc aaa ttt cga ctg aca acc aag ttc         1014
Asp Asp Met Ile Pro Lys Glu Ser Lys Phe Arg Leu Thr Thr Lys Phe
                285                 290                 295 ttt gga acc ttc cta cct gag gtg gcc aag aag ttt ccc aac atg aag         1062
Phe Gly Thr Phe Leu Pro Glu Val Ala Lys Lys Phe Pro Asn Met Lys
            300                 305                 310 ata cag atc cat gtc tca gcc tcc acc ccg cca cac ctg tct gtg cag         1110
Ile Gln Ile His Val Ser Ala Ser Thr Pro Pro His Leu Ser Val Gln
        315                 320                 325 ccc acc ggc ctt acc ttc tac cct gcc gtg gat gtc cag gcc ttt gcc         1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac         1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga         1254
Thr Thr Gly Ser Met Glu Val Ser Ala Glu Ser Asn Arg Leu Val Gly
                365                 370                 375 gag ctc aag ctg gat agg ctg ctc ctg gaa ctg aag cac tca aat att         1302
Glu Leu Lys Leu Asp Arg Leu Leu Leu Glu Leu Lys His Ser Asn Ile
            380                 385                 390 ggc ccc ttc ccg gtt gaa ttg ctg cag gat atc atg aac tac att gta         1350
Gly Pro Phe Pro Val Glu Leu Leu Gln Asp Ile Met Asn Tyr Ile Val
        395                 400                 405 ccc att ctt gtg ctg ccc agg gtt aac gag aaa cta cag aaa ggc ttc         1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag         1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa             1491
Pro His Gln Asn Phe Leu Leu Phe Gly Ala Asp Val Val Tyr Lys
                445                 450                 455 tgaaggcacc agggtgccg ggggctgtca gccgcacctg ttcctgatgg gctgtggggc        1551
accggctgcc tttccccagg gaatcctctc cagatcttaa ccaagagccc cttgcaaact       1611
tcttcgactc agattcagaa atgatctaaa cacgaggaaa cattattcat tggaaaagtg      1671
catggtgtgt attttaggga ttatgagctt cttcaaggg ctaaggctgc agagatattt       1731
cctccaggaa tcgtgtttca attgtaacca agaaatttcc atttgtgctt catgaaaaaa       1791
aacttctggt tttttcatg tg                                                 1813

<210> SEQ ID NO 2
<211> LENGTH: 487
<212> TYPE: PRT
<213> ORGANISM: Homo sapiens

<400> SEQUENCE: 2

Met Arg Glu Asn Met Ala Arg Gly Pro Cys Asn Ala Pro Arg Trp Val
        -30                 -25                 -20

Ser Leu Met Val Leu Val Ala Ile Gly Thr Ala Val Thr Ala Ala Val
-15                 -10                 -5              -1  1

Asn Pro Gly Val Val Val Arg Ile Ser Gln Lys Gly Leu Asp Tyr Ala
                5                   10                  15
```

```
Ser Gln Gln Gly Thr Ala Ala Leu Gln Lys Glu Leu Lys Arg Ile Lys
         20                  25                  30

Ile Pro Asp Tyr Ser Asp Ser Phe Lys Ile Lys His Leu Gly Lys Gly
     35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
        340                 345                 350

Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
        420                 425                 430
```

```
Gln Leu Tyr Asn Val Val Leu Gln Pro His Gln Asn Phe Leu Leu Phe
    435                 440                 445

Gly Ala Asp Val Val Tyr Lys
450                 455

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: artificial
      peptide XMP.365
<220> FEATURE:
<221> NAME/KEY: SITE
<222> LOCATION: (1)..(10)
<223> OTHER INFORMATION: Positions 1-10 are D-amino acids
<220> FEATURE:
<223> OTHER INFORMATION: The C-Terminus is Amidated

<400> SEQUENCE: 3

Lys Trp Leu Ile Gln Leu Phe His Lys Lys
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: artificial
      peptide XMP.391
<220> FEATURE:
<223> OTHER INFORMATION: The C-Terminus is Amidated

<400> SEQUENCE: 4

Lys Val Gly Trp Leu Ile Gln Leu Phe His Lys Lys
  1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: artificial
      peptide XMP.416
<220> FEATURE:
<221> NAME/KEY: SITE
<222> LOCATION: (1)..(10)
<223> OTHER INFORMATION: Positions 1-10 are D-amino acids
<220> FEATURE:
<223> OTHER INFORMATION: The C-Terminus is Amidated
<220> FEATURE:
<223> OTHER INFORMATION: 8-amino-octanyl group; NH2-(CH2)7-CO at
      N-Terminus

<400> SEQUENCE: 5

Lys Trp Leu Ile Gln Leu Phe His Lys Lys
  1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: artificial
      peptide XMP.445
<220> FEATURE:
<221> NAME/KEY: SITE
<222> LOCATION: (1)
<223> OTHER INFORMATION: At position 1, Xaa=D-Lys
<220> FEATURE:
<221> NAME/KEY: SITE
```

```
-continued

<222> LOCATION: (2)
<223> OTHER INFORMATION: At position 2, Xaa=D-Val
<220> FEATURE:
<221> NAME/KEY: SITE
<222> LOCATION: (11)
<223> OTHER INFORMATION: At position 11, Xaa=D-Lys
<220> FEATURE:
<221> NAME/KEY: SITE
<222> LOCATION: (12)
<223> OTHER INFORMATION: At position 12, Xaa=D-Lys

<400> SEQUENCE: 6

Xaa Xaa Gly Trp Leu Ile Gln Leu Phe His Xaa Xaa
 1               5                  10
```

AGENTS AND METHODS FOR INHIBITING $F_1/F_0$ ATPASE

This application claims priority of U.S. Provisional Application No. 60/143,373 filed Jul. 12, 1999, the disclosure of which is incorporated herein by reference.

FIELD OF THE INVENTION

The invention relates generally to the identification of inhibitors of ATP synthase ($F_1/F_0$ ATPase), useful as antimicrobial or anti-proliferative agents.

BACKGROUND OF THE INVENTION

Infectious diseases can be caused by a number of organisms, including bacteria, fungi, protozoans and other parasites, and viruses. Bacteria as a group generally include gram-negative bacteria, gram-positive bacteria, spirochetes, rickettsiae, mycoplasmas, mycobacteria and actinomycetes. Resistance of bacteria and other pathogenic organisms to antimicrobial agents is an increasingly troublesome problem. The accelerating development of antibiotic-resistant bacteria, intensified by the widespread use of antibiotics in farm animals and overprescription of antibiotics by physicians, has been accompanied by declining research into new antibiotics with different modes of action. [*Science*, 264: 360–374 (1994)].

Antibacterial agents can be broadly classified based on chemical structure and proposed mechanism of action, and major groups include the following: (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Protozoa account for a major proportion of infectious diseases worldwide, but most protozoan infections occur in developing countries. Treatment of protozoan infections is hampered by a lack of effective chemotherapeutic agents, excessive toxicity of the available agents, and developing resistance to these agents.

Fungi are not only important human and animal pathogens, but they are also among the most common causes of plant disease. Fungal infections (mycoses) are becoming a major concern for a number of reasons, including the limited number of antifungal agents available, the increasing incidence of species resistant to known antifungal agents, and the growing population of immunocompromised patients at risk for opportunistic fungal infections, such as organ transplant patients, cancer patients undergoing chemotherapy, burn patients, AIDS patients, or patients with diabetic ketoacidosis. The incidence of systemic fungal infections increased 600% in teaching hospitals and 220% in non-teaching hospitals during the 1980's. The most common clinical isolate is *Candida albicans* (comprising about 19% of all isolates). In one study, nearly 40% of all deaths from hospital-acquired infections were due to fungi [Sternberg, *Science*, 266:1632–1634 (1994)].

Known antifungal agents include polyene derivatives, such as amphotericin B (including lipid or liposomal formulations thereof) and the structurally related compounds nystatin and pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer], poscaconazole [SCH56592, Schering-Plough]) and ravuconazole; allylamines-thiocarbamates (including tolnaftate, naftifine and terbinafine); griseofulvin; ciclopirox; haloprogin; echinocandins (including caspofungin [MK-0991, Merck], FK463 [Fujisawa] and VER-002 [Versicor]); nikkomycins; and sordarins. Recently discovered as antifungal agents are a class of products related to bactericidal/permeability-increasing protein (BPI), described in U.S. Pat. Nos. 5,627,153, 5,858,974, 5,652,332, 5,856,438, 5,763,567 and 5,733,872, the disclosures of all of which are incorporated herein by reference.

Bactericidal/permeability-increasing protein (BPI) is a protein isolated from the granules of mammalian polymorphonuclear leukocytes (PMNs or neutrophils), which are blood cells essential in the defense against invading microorganisms. See Elsbach, 1979, *J Biol. Chem.*, 254: 11000; Weiss et al., 1987, *Blood* 69: 652; Gray et al., 1989, *J Biol. Chem.* 264: 9505. The amino acid sequence of the entire human BPI protein and the nucleic acid sequence of DNA encoding the protein (SEQ ID NOS: 1 and 2) have been reported in U.S. Pat. No. 5,198,541 and FIG. 1 of Gray et al., *J. Biol. Chem.*, 264:9505 (1989), incorporated herein by reference. Recombinant human BPI holoprotein has also been produced in which valine at position 151 is specified by GTG rather than GTC, residue 185 is glutamic acid (specified by GAG) rather than lysine (specified by AAG) and residue 417 is alanine (specified by GCT) rather than valine (specified by GTT). An N-terminal fragment of human BPI possesses the anti-bacterial efficacy of the naturally-derived 55 kD human BPI holoprotein. (Ooi et al., 1987, *J Bio. Chem.* 262: 14891–14894). In contrast to the N-terminal portion, the C-terminal region of the isolated human BPI protein displays only slightly detectable anti-bacterial activity against gram-negative organisms and some endotoxin neutralizing activity. (Ooi et al., 1991, *J Exp. Med.* 174: 649). An N-terminal BPI fragment of approximately 23 kD, referred to as $rBPI_{23}$, has been produced by recombinant means and also retains anti-bacterial, including anti-endotoxin activity against gram-negative organisms (Gazzano-Santoro et al., 1992, *Infect. Immun.* 60: 4754–4761). An N-terminal analog designated $rBPI_{21}$, (also referred to as $rBPI(1-193)ala^{132}$) has been described in U.S. Pat. No. 5,420,019.

Three separate functional domains within the recombinant 23 kD N-terminal BPI sequence have been discovered (Little et al., 1994, *J Biol. Chem.* 269: 1865). These functional domains of BPI designate regions of the amino acid sequence of BPI that contributes to the total biological activity of the protein and were essentially defined by the activities of proteolytic cleavage fragments, overlapping 15-mer peptides and other synthetic peptides. Domain I is defined as the amino acid sequence of BPI comprising from about amino acid 17 to about amino acid 45. Initial peptides based on this domain were moderately active in both the inhibition of LPS-induced LAL activity and in heparin binding assays, and did not exhibit significant bactericidal activity. Domain II is defined as the amino acid sequence of BPI comprising from about amino acid 65 to about amino acid 99. Initial peptides based on this domain exhibited high LPS and heparin binding capacity and exhibited significant antibacterial activity. Domain III is defined as the amino acid sequence of BPI comprising from about amino acid 142 to about amino acid 169. Initial peptides based on this domain exhibited high LPS and heparin binding activity and exhibited surprising antimicrobial activity, including antifungal and antibacterial (including, e.g., anti-gram-positive and anti-gram-negative) activity. The biological activities of peptides derived from or based on these functional domains (i.e., functional domain peptides) may include LPS binding, LPS neutralization, heparin binding, heparin neutralization or antimicrobial activity.

Many other utilities of BPI protein products, including rBPI$_{23}$ and rBPI$_{21}$, have been described due to the wide variety of biological activities of these products. For example, BPI protein products are bactericidal for gram-negative bacteria, as described in U.S. Pat. Nos. 5,198,541, 5,641,874, 5,948,408, 5,980,897 and 5,523,288. International Publication No. WO 94/20130 proposes methods for treating subjects suffering from an infection (e.g. gastrointestinal) with a species from the gram-negative bacterial genus Helicobacter with BPI protein products. BPI protein products also enhance the effectiveness of antibiotic therapy in gram-negative bacterial infections, as described in U.S. Pat. Nos. 5,948,408, 5,980,897 and 5,523,288 and International Publication Nos. WO 89/01486 (PCT/US99/02700) and WO 95/08344 (PCT/US94/11255). BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. WO 95/19180 (PCT/US95/00656). BPI protein products exhibit antifungal activity, and enhance the activity of other antifungal agents, as described in U.S. Pat. No. 5,627,153 and International Publication No. WO 95/19179 (PCT/US95/00498), and further as described for BPI-derived peptides in U.S. Pat. No. 5,858,974, which is in turn a continuation-in-part of U.S. application Ser. No. 08/504,841 and corresponding International Publication Nos. WO 96/08509 (PCT/US95/09262) and WO 97/04008 (PCT/US96/03845), as well as in U.S. Pat. Nos. 5,733,872, 5,763,567, 5,652,332, 5,856,438 and corresponding International Publication Nos. WO 94/20532 (PCT/US/94/02465) and WO 95/19372 (PCT/US94/10427). BPI protein products exhibit anti-protozoan activity, as described in U.S. Pat. Nos. 5,646,114 and 6,013,629 and International Publication No. WO 96/01647 (PCT/US95/08624). BPI protein products exhibit anti-chlamydial activity, as described in co-owned U.S. Pat. No. 5,888,973 and WO 98/06415 (PCT/US97/13810). Finally, BPI protein products exhibit anti-mycobacterial activity, as described in co-owned, co-pending U.S. application Ser. No. 08/626,646, which is in turn a continuation of U.S. application Ser. No. 08/285,803, which is in turn a continuation-in-part of U.S. application Ser. No. 08/031,145 and corresponding International Publication No. WO 94/20129 (PCT/US94/02463).

The effects of BPI protein products in humans with endotoxin in circulation, including effects on TNF, IL-6 and endotoxin are described in U.S. Pat. Nos. 5,643,875, 5,753,620 and 5,952,302 and corresponding International Publication No. WO 95/19784 (PCT/US95/01151).

BPI protein products are also useful for treatment of specific disease conditions, such as meningococcemia in humans (as described in U.S. Pat. Nos. 5,888,977 and 5,990,086 and International Publication No. WO97/42966 (PCT/US97/08016), hemorrhage due to trauma in humans, (as described in U.S. Pat. Nos. 5,756,464 and 5,945,399, U.S. application Ser. No. 08/862,785 and corresponding International Publication No. WO 97/44056 (PCT/US97/08941), burn injury (as described in U.S. Pat. No. 5,494,896 and corresponding International Publication No. WO 96/30037 (PCT/US96/02349)) ischemia/reperfusion injury (as described in U.S. Pat. No. 5,578,568), and depressed RES/liver resection (as described in co-owned, co-pending U.S. application Ser. No. 08/582,230 which is in turn a continuation of U.S. application Ser. No. 08/318,357, which is in turn a continuation-in-part of U.S. application Ser. No. 08/132,510, and corresponding International Publication No. WO 95/10297 (PCT/US94/11404).

BPI protein products also neutralize the anticoagulant activity of exogenous heparin, as described in U.S. Pat. No. 5,348,942, neutralize heparin in vitro as described in U.S. Pat. No. 5,854,214, and are useful for treating chronic inflammatory diseases such as rheumatoid and reactive arthritis, for inhibiting endothelial cell proliferation, and for inhibiting angiogenesis and for treating angiogenesis-associated disorders including malignant tumors, ocular retinopathy and endometriosis, as described in U.S. Pat. Nos. 5,639,727, 5,807,818 and 5,837,678 and International Publication No. WO 94/20128 (PCT/US94/02401).

BPI protein products are also useful in antithrombotic methods, as described in U.S. Pat. Nos. 5,741,779 and 5,935,930 and corresponding International Publication No. WO 97/42967 (PCT/US7/08017).

There continues to exist a need for novel antimicrobial agents and anti-proliferative agents and for methods of identifying such novel compounds. Such methods ideally would identify compounds that are unrelated to conventional agents and that target different aspects of cell growth and replication compared to conventional agents.

SUMMARY OF THE INVENTION

One aspect of the present invention provides methods for identifying novel compounds that inhibit the function of $F_1/F_0$ ATPase (also referred to as ATP synthase or ATP synthetase or $F_0/F_1$ ATPase) and that have antimicrobial or anti-proliferative activity, particularly antibacterial activity. Such novel compounds are identified either through screening libraries of existing molecules, such as inorganic or organic compounds (including bacterial, fungal, mammalian, insect or plant products, peptides, peptidomimetics and/or organomimetics) or through rational design of molecules that specifically interfere with the function of the ATP synthase. Novel antimicrobial and/or anti-proliferative compounds identified by such methods are also provided.

It is contemplated that screening methods according to the present invention may involve one or more assays, including an assay for ability of test compounds to inhibit or produce a decrease in the activity of ATP synthase preparations, e.g., as directly measured by ATP hydrolysis or ATP synthesis, or as indirectly measured by oxygen consumption assays, such as changes in the rate of oxygen consumption of mitochondria (e.g., State 3 or State 4) or whole cells, or by assays to detect alterations in electron transport or associated cytochromes, proton gradient, or membrane potential, or by mitochondrial function of whole mitochondria or submitochondrial particles (e.g. by measuring total ATP levels); or an assay for ability of test compounds to interact (including, e.g., ability to bind to or abiltiy to competitively inhibit binding of BPI-derived peptides to) with ATP synthase.

It is further contemplated that screening methods according to the present invention may involve additional screening steps. For example, the screening may include selection of test compounds that have a differential effect on microbial target cells in comparison to other types of cells (e.g., a greater effect on bacterial cells relative to mammalian cells, or a greater effect on bacterial cells relative to fungal cells). Suitable candidate compounds may have a 2-fold or more, 10-fold or more, 50-fold or more, or 100-fold or more separation between target cell activity and other cell toxicity. Final stages of screening for antimicrobial or antiproliferative agents may include conventional testing for in vitro and/or in vivo activity against a variety of organisms using procedures known in the art.

According to this aspect of the invention, methods are provided for identifying a potential or candidate antimicrobial compound comprising the steps of: (a) selecting a test compound that interacts with or that produces a decrease in the activity of an $F_1/F_0$ ATP synthase (e.g., a bacterial cell $F_1/F_0$ ATP synthase, or a protozoan/parasite mitochondrial ATP synthase, or fungal or mammalian mitochondrial ATP synthase); and (b) detecting inhibition of growth of microbial target cells in the presence of the selected test compound from step (a). Step (a) can be carried out, for example,. by determining $F_1/F_0$ ATP synthase activity in the presence and absence of the test compound followed by selecting test compounds that inhibit or produce a decrease in the activity. Step (b) can be carried out, for example, by detecting growth of microbial target cells in the presence and absence of the test compound, followed by selecting a test compound that inhibits growth.

The $F_1/F_0$ ATP synthase need not be, but is preferably from the microbial target cell. Alternatively, a mammalian or other eukaryotic mitochondrial $F_1/F_0$ ATP synthase could be used. For example, oxygen consumption of mammalian or other eukaryotic mitochondria can be measured in step (a).

Optionally, another screening step (c) is utilized (instead of, concurrent with, or subsequent to step (b)) that involves detecting a reduction in total ATP levels of the microbial target cell or its mitochondria in the presence of the selected test compound compared to the absence of the test compound. Preferably an additional screening step is utilized that involves detecting growth of a non-target cell (e.g., a mammalian cell) in the presence and absence of the selected test compound.

Another aspect of the invention involves selecting a test compound that produces a decrease in total ATP levels of microbial cells or their mitochondria, relative to ATP levels in the absence of the test compound, followed by an additional screening step such as detecting growth of microbial target cells, and/or detecting growth of non-target cells.

Another aspect of the invention provides methods of identifying antimicrobial compounds by assaying for ability to uncouple electron transport from ATP synthesis, e.g., by measuring oxygen consumption of whole cells, mitochondria or bacterial membrane preparations in the presence and absence of the test compound followed by measuring oxygen consumption after further addition of a known uncoupling agent, preferably at the maximally effective uncoupling concentration of both the test compound and the known uncoupling agent. If the test compound is an uncoupling agent, addition of the known uncoupling agent will produce no significant increase in oxygen consumption. Such assay steps can be combined with other assays disclosed herein and preferably are combined with selection of test compounds that have a differential effect on target cells in comparison to other types of cells.

Specifically provided are the use of such screening methods to identify novel antimicrobial agents that are active against pathogenic organisms that rely on ATP synthase for aerobic metabolism, for example, gram-negative bacteria, gram-positive bacteria, Mycoplasma, Mycobacteria, protozoa, or other prokaryotes. Also specifically provided are the use of such screening methods to identify novel insecticidal agents or novel herbicidal agents that are active against, for example, plant organisms (including weeds or algae).

Another aspect of the invention provides methods for treating infections involving pathogenic organisms that rely on ATP synthase for aerobic metabolism (for example, gram-negative bacteria, gram-positive bacteria, Mycoplasma, protozoa, or other prokaryotes or parasites) by inhibiting the activity of ATP synthase, using compounds other than those presently known in the art, such as BPI protein products or BPI-derived peptides previously known in the art. Concurrent administration of other conventional antimicrobial agents is contemplated.

A further aspect of the invention provides methods for killing or inhibiting growth of insects or plants by inhibiting the activity of their respective ATP synthases. Preferred methods involve administration of BPI protein products, including BPI-derived peptides.

Corresponding screening methods for identifying antifungal agents, as well as novel agents and therapeutic uses made possible by these methods, are addressed in U.S. Provisional Application Ser. No. 60/143,372 filed Jul. 12, 1999 and corresponding co-owned, concurrently filed U.S. application Ser. No. 09/543,802, both of which are incorporated herein by reference. According to yet another aspect of the invention, the discovery that BPI protein products, particularly BPI-derived peptides, also inhibit mammalian mitochondrial ATP synthase activity provides a basis for use of these compounds, alone or in association with appropriate targeting agents, as anti-proliferative or cytotoxic agents that can be used to treat conditions for which an inhibition of cellular proliferation is desirable, including cancer or other neoplastic diseases, autoimmune diseases, etc.

Numerous additional aspects and advantages of the invention will become apparent to those skilled in the art upon consideration of the following detailed description of the invention which describes presently prepared embodiments thereof.

DETAILED DESCRIPTION OF THE INVENTION

Figure 1:
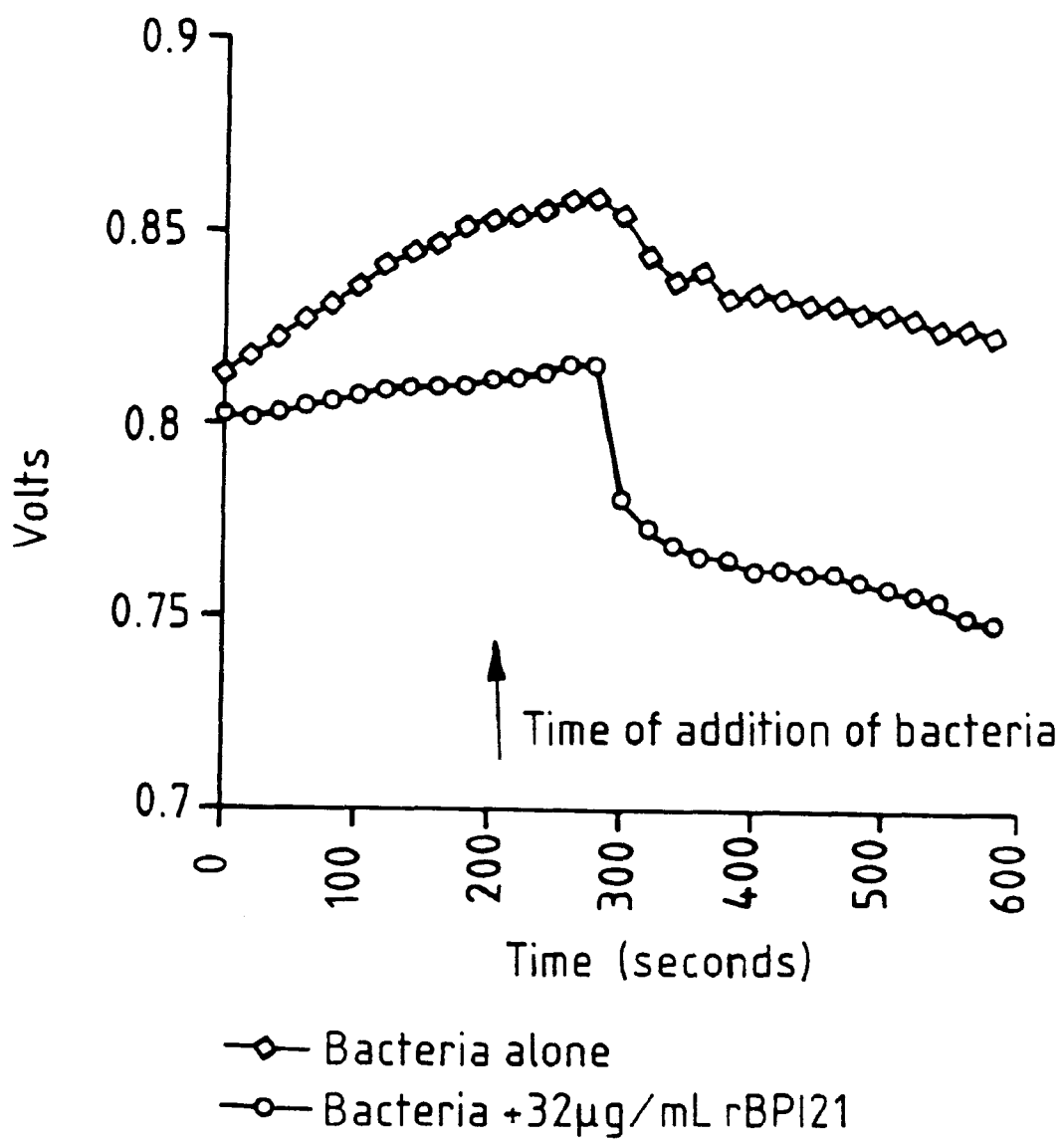
FIG. 1 shows the effect of antibacterial BPI protein product $rBPI_{21}$ on the activity of bacterial ATP synthase as measured by oxygen consumption.

The invention is based on the discovery that a class of antimicrobial agents derived from bactericidal/permeability-increasing protein (BPI) acts by a unique mechanism involving inhibition of ATP synthase ($F_1/F_0$ ATPase). Members of the $F_1/F_0$ family of ATP synthases are present in bacteria, in chloroplast membranes, and in mitochondria. [*Molecular Biology of the Cell*, Alberts et al., eds., Garland Publishing, Inc., New York (1983), pages 484–510.] The enzyme is well conserved; the β subunit polypeptides from different sources show exceptionally strong sequence homology (almost 50% sequence identity), while the minor $F_1$ subunit polypeptides show more sequence and size variation. In fact, in the highly conserved regions of the β subunit, the primary amino acid sequences were identical among tobacco, spinach, maize, bovine, *E. coli* and *S. cerevisiae*. [Takeda et al., *J Biol. Chem.*, 260(29):15458–15465 (1985)].

In the *E. coli* ATP synthase, the membrane integral $F_0$ portion is composed of three different subunits, a, b (2 copies) and c (9–12 copies), and the membrane peripheral $F_1$ portion is composed of five different subunits, α (3 copies), β (3 copies), γ, δ and ε. ATP synthase activity can be reconstituted from purified α, β and γ subunits. Crystal structure analysis of the bovine mitochondria ATP synthase $F_1$ portion showed that it is composed of three copies of subunit α and three copies of subunit β that are arranged alternately in a hexagonal ring and form three nucleotide binding catalytic sites around the γ subunit, which then appears to rotate like a crankshaft through the three catalytic stages of hydrolysis. Subunits δ and ε are required for binding of the $F_1$ and $F_0$ components and are likely at the interface of the two components. Subunits δ and b have been shown to interact, as have subunits γ and c and subunits ε and c. In *E. coli*, the 12 proteolipid c subunits of the proton translocating $F_0$ component are postulated to be arranged in a ring-like structure that forms a torque generating rotatory engine. [Junge et al., *TIBS*, 22: 420–423 (1997); Boyer et al., *Annu. Rev. Biochem.*, 66:717–49 (1997); Caviston et al., *FEBS Lett.*, 429:201–206 (1998); Weber et al., *Biochim. Biophys. Acta*, 1319:19–58 (1997)].

Three separate functional domains within the recombinant 23 kD N-terminal BPI sequence have been discovered (Little et al., 1994, *J. Biol. Chem.* 269: 1865). These functional domains of BPI designate regions of the amino acid sequence of BPI that contributes to the total biological activity of the protein and were essentially defined by the activities of proteolytic cleavage fragments, overlapping 15-mer peptides and other synthetic peptides. Domain I is defined as the amino acid sequence of BPI comprising from about amino acid 17 to about amino acid 45. Initial peptides based on this domain were moderately active in both the inhibition of LPS-induced LAL activity and in heparin binding assays, and did not exhibit significant bactericidal activity. Domain II is defined as the amino acid sequence of BPI comprising from about amino acid 65 to about amino acid 99. Initial peptides based on this domain exhibited high LPS and heparin binding capacity and exhibited significant antibacterial activity. Domain III is defined as the amino acid sequence of BPI comprising from about amino acid 142 to about amino acid 169. Initial peptides based on this domain exhibited high LPS and heparin binding activity and exhibited surprising antimicrobial activity, including antifungal or antibacterial (including, e.g., anti-gram-positive or anti-gram-negative) activity. The biological activities of peptides derived from or based on these functional domains (i.e., functional domain peptides) may include LPS binding, LPS neutralization, heparin binding, heparin neutralization or antimicrobial activity.

As used herein, "BPI-derived peptides" include "Domain III derived peptides", for example, peptides having an amino acid sequence of BPI protein from about position 142 to about position 169 (Domain III), subsequences thereof, variants of the sequence or subsequence, or reverse sequences or subsequences or variants thereof, which possess antimicrobial activity. Specifically included are those antimicrobial peptides having six to fourteen amino acids and having the amino acid sequence of BPI protein from about position 148 to about position 161, subsequences thereof or variants of the sequence or subsequence. Certain preferred peptides have fourteen amino acids and among the preferred variant sequences and subsequences are those having K as an amino acid substituted for G at position 152. Preferred peptide sequences with fourteen amino acids have a core amino acid sequence. Preferred variant sequence peptides include those wherein at least one or most preferably two of each BPI L-amino acid sequence residue on the N- and C-termini has been replaced by a D-isomer amino acid. Variants involving BPI sequence replacements by atypical amino acids (e.g., (1-naphthyl)A, (2-naphthyl)A, para-amino F, cyclohexyl A, - or -aminobutyric acids, methyl A or N-methyl G, V or L) are also included within this group.

One aspect of the present invention provides methods for identifying an antimicrobial or anti-proliferative compound that includes the step of specifically determining (i.e., measuring qualitatively or quantitatively, directly or indirectly) the activity of an ATP synthase in the presence of a test compound, wherein a decreased activity (relative to activity in the absence of the test compound) indicates that the test compound inhibits or interferes with the activity of the ATP synthase.

Suitable ATP synthase preparations that may be used include "isolated" preparations. "Isolated" means removed from its natural milieu, e.g., an isolated bacterial ATP synthase is a preparation of ATP synthase that is no longer part of an intact bacterial cell. Isolated ATP synthase preparations include isolated whole mitochondria, submitochondrial particles or vesicles, isolated membrane-bound ATP synthase, isolated soluble ATP synthase, isolated subunits thereof (which may be isolated by conventional purification methods or may be assembled from purified or recombinantly produced polypeptide components), or isolated or recombinantly produced polypeptide components of such subunits. See, e.g., Caviston et al., *FEBS Lett.*, 429:201–206 (1998); Deisinger et al., *Eur. J. Biochem.*, 218:377–383 (1993) (preparation of mitochondrial vesicles); Alfonzo et al., *J Bioenerg Biomembr*, 13(5–6):375–91 (1981) (isolation of the hydrophobic portion of the mitochondrial ATP synthase); and Moradi-Ameli et al., *Biochim Biophys Acta*, 890(1):55–65 (1987) (purified membrane-bound mitochondrial -ATPase and a beta subunit thereof).

Sources for test compounds to be screened include (1) inorganic or organic chemical libraries, (2) natural product libraries, or (3) combinatorial libraries comprised of either random or mimetic peptides, oligonucleotides or organic molecules. Chemical libraries may be readily synthesized or purchased from a number of commercial sources, and may include structural analogs of known compounds or compounds that are identified as "hits" or "leads" via natural product screening. The sources of natural product libraries are collections of microorganisms (including bacteria or fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and/or variants (nonnaturally occurring) variants thereof. For a review, see *Science* 282:63–68 (1998). Combinatorial libraries are composed of large numbers of peptides, oligonucleotides or organic compounds and can be readily prepared by traditional automated synthesis methods, PCR, cloning or proprietary synthetic methods. Of particular interest are peptide or oligonucleotide combinatorial libraries. Still other libraries of interest include peptide, protein, peptidomimetic, multiparallel synthetic collection, recombinatorial, or polypeptide libraries. For a review of combinatorial chemistry and libraries created therefrom, see Myers, *Curr. Opin. Biotechnol.* 8:701–707(1997). For reviews and examples of peptidomimetic libraries, see Al-Obeidi et al., *Mol. Biotechnol,* 9(3):205–23 (1998); Hruby et al., *Curr Opin Chem Biol,* 1(1):114–19 (1997); Dorner et al., *Bioorg Med Chem,* 4(5):709–15 (1996) (alkylated dipeptides). A variety of companies have constructed chemical libraries and provide their use for screening, including for example, 3-Dimensional Pharmaceuticals, Exton, Pa.; Agouron Pharmaceutical, La Jolla, Calif.; Alanex Corp., San Diego, Calif.; Ariad Pharmaceuticals, Cambridge, Mass.; ArQule, Inc., Medford, Mass.; Arris Pharmaceutical, S. San Francisco, Calif.; Axys, S. San Francisco, Calif.; Biocryst Pharmaceuticals, Birmingham, Ala.; Cadus Pharmaceuticals, Tarrytown, N.Y.; Cambridge Combinatorial, Cambridge, UK; ChemGenics, Cambridge, Mass.; CombiChem, San Diego, Calif.; Corvas International, San Diego, Calif.; Cubist Pharmaceuticals, Cambridge, Mass.; Darwin Molecular, Bothell, Wash.; Houghten Pharmaceuticals, San Diego, Calif.; Hybridon, Cambridge, Mass.; Isis Pharmaceuticals, Carlsbad, Calif.; Ixsys, San Diego, Calif.; Molecumetics, Bellevue, Wash.; Peptide Therapeutics, Cambridge, UK; Pharmacopia, Princeton, N.J.; SUGEN, Redwood City, Calif.; Telik, Inc., S. San Francisco, Calif.; or Tripos, Inc., St. Louis, Mo.

Inhibition of or decrease in ATP synthase activity may be determined in a variety of ways, including directly via measurement of ATP hydrolysis, ATP synthesis, or indirectly by oxygen consumption assays, such as changes in the rate of oxygen consumption of mitochondria (e.g., State 3 or State 4) or whole cells, or by assays to detect alterations in electron transport or associated cytochromes or proton gradient or membrane potential, or by mitochondrial function of whole mitochondria or submitochondrial particles (e.g., by measuring total ATP levels).

The ATP hydrolysis (phosphatase) activity of the ATP synthase can be determined by any methods known in the art. See, e.g., Guerrieir et al. in *Organelles in eukaryotic cells,* Tager et al., eds., Plenum Press, New York and London (1989), pages 197–208; Pullman et al., *J. Biol. Chem.,* 235:3822–3829; Fiske and Subbarow, *J. Biol. Chem.,* 81:629–679 (1929); Ames, *Methods Enzymol.,* 8:115–118 (1966); Brown, in *Red Cell Membranes-A methodological approach,* Ellory and Young, eds, Academic Press, New York (1982), pages 223–228; King, *Methods Cell. Biol.,* 47:141–145 (1995); Kagami et al., *Methods Cell. Biol.,* 47:147–150 (1995); Henkel et al., *Anal. Biochem.,* 169:312–318 (1988); Rieger et al., *Anal. Biochem.,* 246:86–95 (1997); Ausubel et al., eds., *Current Protocols in Molecular Biology,* Greene Publishing Associates and Wiley-Interscience, New York, sec. 18.5.5; and Hayes, ed., *Principles and Methods of Toxicology,* Raven Press, New York (1984), pages 597–608; all of which are incorporated by reference herein. Law et al., *Methods Enzymol.,* 260:133–163 (1995), incorporated by reference herein, describes a variety of alternative methods for evaluating the activity of ATP synthase, such as measurement of ATP synthase activity by coupling the ATP synthesis reaction to NADH oxidation, measurement of cellular respiration parameters, such as measurement of oxygen consumption [see also Fowler et al., in Principles and Methods of Toxicology, Hayes, ed., Raven Press, NY, pages 635–642 (1982)], or measurement of ATP synthesis activity via incorporation of labeled phosphate (e.g., with a radioisotope or a fluorescent label) into ATP. ATP hydrolysis or synthesis can also be determined by measuring ATP levels using luciferase-luciferin, according to which the availability of highly sensitive light photomultipliers permits the detection of extremely low concentrations of ATP. In the presence of ATP and oxygen, luciferase converts luciferin to oxyluciferin in a reaction that emits light detectable by a bioluminometer or fluorimeter. See, e.g., Lemasters et al., *Methods Enzymol.,* 56:530–544 (1979); "Bioluminescent Determination of ATP with Luciferase-Luciferin," Sigma Biochemical Technical Bulletin No. BL-100, November 1991. Membrane potential may optionally be assayed using a tetraphenyl phosphonium ion (TPP+) electrode as described in Westernoff et al., *Proc. Nat'l Acad. Sci. USA,* 86:6597–6601 (1989), which describes use of a device fitted with oxygen, TPP+ and salicylate electrodes to detect a release of TPP+ that indicates a decrease in membrane potential.

The effect of test compounds on ATP synthase activity of whole cells can also optionally be assayed using any membrane potential indicator dye or metabolic oxidation-reduction indicator dye known in the art. See Loew, Chapter 8 in *Biomembrane Electrochemistry,* Blank and Vodyanoy, eds., American Chemical Society, Washington, DC (1994), pages 151–173. Particularly preferred dyes are membrane potential dyes such as $DiOC_6(3)$, JC-1, rhodamine 123, or MitoTracker® reduced dyes [Molecular Probes, Eugene, Oreg.]. Antimicrobial compounds such as $rBPI_{21}$ or BPI-derived peptide XMP.365 (SEQ ID NO: 3) produce a characteristic pattern of accumulation in cells of membrane potential dye in a peptide concentration-dependent manner, with retention of the dye notwithstanding an onset of loss or reduction of organism viability at the same peptide concentration. Test compounds that produce a pattern similar to that exhibited by antimicrobial BPI protein products are selected for further testing. Other preferred dyes are metabolic oxidation-reduction indicator dyes such as Alamar Blue™ [AccuMed Int'l, Westlake, Ohio]. Antimicrobial compounds such as $rBPI_{21}$ or BPI-derived peptides XMP.365 (SEQ ID NO: 3) or XMP.391 (SEQ ID NO: 4) or XMP.416 (SEQ ID NO: 5) produce a characteristic pattern of increased metabolic oxidation-reduction activity relative to control cells at a less than fully cytotoxic concentration of test compound. Test compounds that produce a pattern similar to that exhibited by antimicrobial BPI protein products are selected for further testing. See U.S. Provisional Application Ser. No. 60/143,290 filed Jul. 12, 1999 and corresponding co-owned, concurrently filed U.S. application Ser. No. 09/543,955, both of which are incorporated herein by reference and U.S. Provisional Application Ser. No. 60/143,485 filed Jul. 12, 1999 and corresponding U.S. application Ser. No. 09/404, 926 filed Sep. 24, 1999 and International Application No. PCT/US99/22361 filed Sep. 24, 1999, all of which are incorporated herein by reference. Iterative screening for compound selection may employ one or combination of assays for testing.

Preferably the compounds that are preliminarily identified by these screening methods are then assayed by conventional methods known in the art for the ability to kill or inhibit growth/replication of whole cells or organisms in vitro. For example, gram-negative bacterial species that may be tested include Acidaminococcus, Acinetobacter, Aeromonas, Alcaligenes, Bacteroides, Bordetella, Branhamella, Brucella, Calymmatobacterium, Campylobacter, Cardiobacterium, Chromobacterium, Citrobacter, Edwardsiella, Enterobacter, Escherichia, Flavobacterium, Francisella, Fusobacterium, Haemophilus, Klebsiella, Legionella, Moraxella, Morganella, Neisseria, Pasturella, Plesiomonas, Porphyromonas, Prevotella, Proteus, Providencia, Pseudomonas, Salmonella, Serratia, Shigella, Streptobacillus, Treponema, Veillonella, Vibrio, or Yersinia species as well as Chlamydia; while gram-positive bacterial species that may be tested include Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, or Corynebacterium species as well as Mycoplasma, Ureaplasma, or Mycobacteria.

Protozoa include Plasmodia, Toxoplasma, Leishmania, Trypanosoma, Giardia, Entamoeba, Acanthamoeba, Nagleria, Hartmanella, Balantidium, Babesia, Cryptosporidium, Isospora, Microsporidium, Trichomonas or Pneumocystis species; other parasites include helminths.

Some compounds may be more suitable for in vitro use, e.g., use as a preservative or decontaminant for fluids or surfaces, or use to sterilize surgical or other medical equipment or implantable devices, either ex vivo or in situ, including prosthetic joints or indwelling invasive devices such as intravenous lines or catheters which are often foci of infection, or use in the preparation of growth media for non-target cells.

Antimicrobial compounds identified by the preliminary screening method are also preferably assayed for effect on mammalian mitochondrial ATP synthase. Ideally, the most desirable compounds for in vivo administration to treat mammals will have a differential effect on target and mammalian cells, i.e., if the compound does affect mitochondrial ATP synthase in intact mammalian cells, a higher concentration of the compound would be required to affect the ATP synthase of mammalian cells than that required to affect the ATP synthase of target cells, thereby allowing therapeutic administration of the compound without undesirable toxic effects. This differential effect could be due, for example, to differences in penetration through the mammalian cell plasma membrane compared to the microbial membrane, differences in affinity for the ATP synthases, or differences in effects on ATP synthase function.

The growth inhibitory (or toxic) effect of test compounds on mammalian cells may be determined through their effect on proliferation, viability or metabolic activity of mammalian cells, using any methods known in the art, e.g., by measuring uptake of tritiated amino acids or nucleotides, by using viability dyes such as propodium iodide or trypan blue; or by using metabolic dyes such as Alamar Blue™ or membrane potential indicator dyes such as such as $DiOC_6$(3), JC-1, rhodamine 123, or Mito Tracker® reduced dyes. For example, when a membrane potential indicator dye assay is conducted on mammalian cells, test compounds with low mammalian cell toxicity are not expected to produce a substantial change in dye fluorescence. Dye-based assays may readily be carried out using fluorescence activated cell sorting (FACS) procedures.

Additionally assays may be performed to evaluate in vitro or in vivo oral availability of the test compound or in vivo oral activity of the test compound as evidenced by activity when administered orally in a comparative survival study.

Assays for oral availability are described in co-owned U.S. Provisional Application Ser. No.60/143,485 filed Jul. 12, 1999 and corresponding U.S. application Ser. No. 09/404, 926 filed Sep. 24, 1999 and International Application No. PCT/US99/22361 filed Sep. 24, 1999, all of which are incorporated herein by reference.

Candidate antimicrobial compounds may also be evaluated for their effect in in vivo models of infection (including infection involving any of the organisms listed above) in normal or immunocompromised animals, using any models known in the art. Exemplary animal models of fungal infection are described in Example 4 of U.S. Pat. No. 5,858,974 and may be modified for any fungal species (including Candida, Aspergilus or Fusarium). Exemplary animal models of bacterial infection are described in U.S. Pat. Nos. 5,523,288 and 5,578,572, incorporated herein by reference, and may be modified for any bacterial species. Exemplary animal models of protozoan infection include those described in U.S. Pat. Nos. 5,646,114, incorporated herein by reference. Other microbial infection models are known in the art. The most desirable compounds for non-topical therapeutic use have an acceptable therapeutic window and are capable of preventing the establishment of an infection or reversing the outcome of an infection once it is established without excessive toxicity.

Optionally, screening methods employ a screening step that detects ability of a test compound to interact with or regulate ATP synthase complex. Test compounds may be screened for ability to bind to or interact with the same site on ATP synthase as BPI protein products, including BPI-derived peptides. For example, direct binding of a test compound to the ATP synthase may be detected through physical or analytical methods known in the art, or alternatively, ability to competitively inhibit binding of BPI protein products, including BPI-derived peptides, to the ATP synthase may be determined by contacting ATP synthase with a test compound and a BPI protein product (one of which is labeled) and measuring binding of the labeled compound.

The invention further provides novel antimicrobial compounds, particularly antibacterial compounds, identified by the methods described herein, as well as methods for treating a subject suffering from infection, particularly bacterial infection, involving administration of such novel antimicrobial compounds. In particular, compounds that interfere with the expression of the ATP synthase include antisense polynucleotides complementary to gene sequences encoding the component polypeptides of the ATP synthase complex, while compounds that interfere with the function of the target ATP synthase include variants of the ATP synthase or ligands of the ATP synthase or variants thereof. The invention further provides transgenic plants that produce antimicrobial compounds, including polynucleotide or polypeptide compounds, that interfere with the expression or function of the target ATP synthase.

"Variants," as used herein, includes polynucleotides or polypeptides which contain one or more deletions, insertions or substitutions, as long as the variant retains substantially the same activity of the wild-type polynucleotide or polypeptide. With regard to polypeptides, deletion variants are contemplated to include fragments lacking portions of the polypeptide not essential for biological activity, and insertion variants are contemplated to include fusion polypeptides in which the wild-type polypeptide or fragment thereof have been fused to another polypeptide.

The use of antimicrobial compounds identified by the screening methods of the present invention is contemplated for the treatment of subjects suffering from microbial infection, especially mammalian subjects such as humans, but also including farm animals such as cows, sheep, pigs, horses, goats or poultry (e.g., chickens, turkeys, ducks or geese), companion animals such as dogs or cats, exotic and/or zoo animals, or laboratory animals including mice, rats, rabbits, guinea pigs, or hamsters. Treatment of infection of plants is also contemplated. "Treatment" as used herein encompasses both prophylactic and/or therapeutic treatment, and may be accompanied by concurrent administration of other antimicrobial agent(s), including any of the agents discussed herein.

Therapeutic compositions may be administered systemically or topically. Systemic routes of administration include oral, intravenous, intramuscular or subcutaneous injection (including into a depot for long-term release), intraocular or retrobulbar, intrathecal, intraperitoneal (e.g. by intraperitoneal lavage), intrapulmonary (using powdered drug, or an aerosolized or nebulized drug solution), or transdermal. Suitable dosages include doses ranging from 1 $\mu$g/kg to 100 mg/kg per day or doses ranging from 0.1 mg/kg to 20 mg/kg per day.

Topical routes include administration in the form of salves, creams, jellies, ophthalmic drops or ointments (as described in co-owned, co-pending U.S. application Ser. Nos. 08/557,289 and 08/557,287, both filed Nov. 14, 1995), ear drops, suppositories, irrigation fluids (for, e.g., irrigation of wounds) or medicated shampoos. For example, for topical administration in drop form, about 10 to 200 $\mu$L of a therapeutic composition may be applied one or more times per day as determined by the treating physician.

For polypeptide therapeutics that are amenable to administration via gene therapy, methods of delivering suitable genes to a subject (including plants or animals) are contemplated.

Those skilled in the art can readily optimize effective dosages and administration regimens for therapeutic compositions as determined by good medical practice and the clinical condition of the individual subject.

"Concurrent administration," or "co-administration," as used herein includes administration of one or more agents, in conjunction or combination, together, or before or after each other. The agents may be administered by the same or by different routes. If administered via the same route, the agents may be given simultaneously or sequentially, as long as they are given in a manner sufficient to allow all agents to achieve effective concentrations at the site of action.

Known antifungal agents include polyene derivatives, such as amphotericin B (including lipid or liposomal formulations thereof) or the structurally related compounds nystatin or pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer], poscaconazole [SCH56592, Schering-Plough]) or ravuconazole; allylamines-thiocarbamates (including tolnaftate, naftifine or terbinafine); griseoflilvin; ciclopirox; haloprogin; echinocandins (including caspofungin [MK-0991, Merck], FK463 [Fujisawa], or VER-002 [Versicor]); nikkomycins; or sordarins. Recently discovered as antifungal agents are a class of products related to bactericidal/permeability-increasing protein (BPI), described in U.S. Pat. Nos. 5,627,153, 5,858,974, 5,652,332, 5,856,438, 5,763,567 and 5,733,872, the disclosures of all of which are incorporated herein by reference.

The polyene derivatives, which include amphotericin B or the structurally related compounds nystatin or pimaricin, are broad-spectrum antifungals that bind to ergosterol, a component of fungal cell membranes, and thereby disrupt the membranes. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated antifungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The azole derivatives impair synthesis of ergosterol and lead to accumulation of metabolites that disrupt the function of fungal membrane-bound enzyme systems (e.g., cytochrome P450) and inhibit fungal growth. This group of agents includes ketoconazole, clotrimazole, miconazole, econazole, butoconazole, oxiconazole, sulconazole, tioconazole, terconazole, fluconazole or itraconazole. Significant inhibition of mammalian P450 results in significant drug interactions. Some of these agents may be administered to treat systemic mycoses. Ketoconazole, an orally administered imidazole, is used to treat nonmeningeal blastomycosis, histoplasmosis, coccidioidomycosis or paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole that is used for oral and esophageal candidiasis and cryptococcal meningitis. Miconazole is a parenteral imidazole with efficacy in coccidioidomycosis and several other mycoses, but has side effects including hyperlipidemia and hyponatremia.

The allylamines-thiocarbamates are generally used to treat skin infections. This group includes tolnaftate, naftifine or terbinafine. Another antifungal agent is griseofulvin, a fungistatic agent which is administered orally for fungal infections of skin, hair or nails that do not respond to topical treatment. Other topical agents include ciclopirox or haloprogin. Yet another topical agent is butenafine (Syed et al., *J. Dermatol.*, 25:648–652 (1988)). [Chapter 49 in Goodman and Gilman, *The Pharmacological Basis of Therapeutics*, 9th ed., McGraw-Hill, New York (1996), pages 1175–1190].

BPI protein products, a class of products related to bactericidal/permeability-increasing protein (BPI), are described in U.S. Pat. No. 5,627,153 and corresponding International Publication No. WO 95/19179 (PCT/US95/00498), all of which are incorporated by reference herein, to have antifungal activity. BPI-derived peptides with antifungal activity are described in U.S. Pat. No. 5,858,974, which is in turn a continuation-in-part of U.S. application Ser. No. 08/504,841 filed Jul. 20, 1994 and corresponding International Publication Nos. WO 96/08509 (PCT/US95/09262) and WO 97/04008 (PCT/US96/03845), all of which are incorporated by reference herein. Other peptides with antifungal activity are described in U.S. Pat. Nos. 5,652,332 and 5,856,438 [corresponding to International Publication No. WO 95/19372 (PCT/US94/10427)], and in U.S. Pat. Nos. 5,763,567 and 5,733,872 [corresponding to International Publication No. WO 94/20532 (PCT/US94/02465)], which is a continuation-in-part of U.S. patent application Ser. No. 08/183,222 filed Jan. 14, 1994, which is a continuation-in-part of U.S. patent application Ser. No. 08/093,202 filed Jul.

15, 1993 [corresponding to International Publication No. WO 94/20128 (PCT/US94/02401)], which is a continuation-in-part of U.S. patent application Ser. No. 08/030,644 filed Mar. 12, 1993, now U.S. Pat. No. 5,348,942, the disclosures of all of which are incorporated herein by reference.

Known antibacterial agents include antibiotics, which are natural chemical substances of relatively low molecular weight produced by various species of microorganisms, such as bacteria (including Bacillus species), actinomycetes (including Streptomyces) or fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the β-lactams, including the penicillins, cephalosporins or monobactams; (2) the aminoglycosides, e.g., gentamicin, tobramycin, netilmycin, or amikacin; (3) the tetracyclines; (4) the sulfonamides and/or trimethoprim; (5) the fluoroquinolones, e.g., ciprofloxacin, norfloxacin, or ofloxacin; (6) vancomycin; (7) the macrolides, which include for example, erythromycin, azithromycin, or clarithromycin; and (8) other antibiotics, e.g., the polymyxins, chloramphenicol or the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, or vancomycin; (2) agents affecting the cell membrane or exerting a detergent effect, such as colistin, novobiocin or polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, or the macrolide antibiotics such as erythromycin or oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, or the tuberculostatic agents isoniazid or para-aminosalicylic acid. Some agents may have more than one primary mechanism of action, especially at high concentrations. In addition, secondary changes in the structure or metabolism of the bacterial cell often occur after the primary effect of the antimicrobial drug.

The penicillins have a characteristic double-ring system composed of a β-lactam ring, which provides the antibacterial activity, and a thiazolidene ring. The penicillins are differentiated by a single side chain that is unique for each penicillin. The compounds are bactericidal and act by inhibiting bacterial transpeptidase, an enzyme involved in synthesis of the bacterial cell wall. Because of their mechanism of action, penicillins are generally active against growing, but not resting, cells. Penicillins, especially penicillin G, have largely gram-positive activity; the relative insensitivity of gram-negative rods to penicillin G and several other penicillins is probably due to the permeability barrier of the outer membrane of gram-negative bacteria. Ampicillin, carbenicillin, ticarcillin, and some other penicillins are active against gram-negative bacteria because they can pass through this outer membrane. Penicillins have relatively few adverse effects, the most important of which are the hypersensitivity (allergic) reactions. These compounds are widely distributed in the body, but do not enter cells and do not usually accumulate in CSF.

Bacterial resistance to the penicillins is by production of the enzyme β-lactamase, which catalyzes hydrolysis of the β-lactam ring. The percentage of bacteria resistant to penicillin has risen to about 80%. Several penicillins, including methicillin, oxacillin, cloxacillin, dicloxacillin or nafcillin, are not affected by the β-lactamase of staphylococci. These antibiotics are useful against most β-lactamase-producing species of Staphylococcus. However, a small number of species are resistant even to these penicillins. Some penicillins, amoxicillin and ticarcillin, are marketed in combination with clavulanic acid, which is a β-lactamase inhibitor that covalently binds to the enzyme and prevents it from hydrolyzing the antibiotics. Another inhibitor, sulbactam, is marketed in combination with ampicillin.

The cephalosporins are characterized by a β-lactam ring, like the penicillins, but have an adjacent dihydrothiazine ring instead of a thiazolidene ring. For convenience, these compounds are generally classified by generations. The first generation includes cephalothin, cephapirin, cefazolin, cephalexin, cephradine or cefadroxil. These drugs generally have excellent gram-positive activity except for enterococci and methicillin-resistant staphylococci, and have only modest gram-negative coverage. The second generation includes cefamandole, cefoxitin, ceforanide, cefuroxime, cefuroxime axetil, cefaclor, cefonicid or cefotetan. This generation generally loses some gram-positive activity by weight and gains limited gram-negative coverage. The third generation includes cefotaxime, moxalactam, ceftizoxime, ceftriaxone, cefoperazone or ceftazidime. These compounds generally sacrifice further gram-positive activity by weight but gain substantial gram-negative coverage against Enterobacter and sometimes are active against Pseudomonas. The cephalosporins bind to penicillin-binding proteins with varying affinity. Once binding occurs, protein synthesis is inhibited. Cephalosporins are usually well tolerated; adverse effects include hypersensitivity reactions and gastrointestinal effects. Cephalosporins may interact with nephrotoxic drugs, particularly aminoglycosides, to increase toxicity. Resistance to cephalosporins is mediated by several mechanisms, including production of β-lactamase, although some strains that do not produce β-lactamase are nevertheless resistant.

Imipenem is a N-formimidoyl derivative of the mold product thienamycin. It contains a β-lactam ring and somewhat resembles penicillin except for differences in the second ring. It has activity against both gram-positive and gram-negative organisms and is resistant to most β-lactamases, although not those from Pseudomonas. It is marketed in combination with cilastin, a compound that inhibits inactivation of imipenem in the kidney by renal dihydropeptidase I enzyme. Cilastin increases the concentration of imipenem in urine, although not in blood.

Aztreonam is the first of a new group of antibiotics referred to as the monobactams. These agents have a β-lactam ring but lack the second ring characteristic of the penicillins and cephalosporins. It acts by binding to penicillin-binding proteins, and produces long, filamentous bacterial shapes that eventually lyse. Aztreonam is active only against aerobic gram-negative bacteria, is susceptible to inactivation by some β-lactamases, and has few adverse effects.

The aminoglycosides contain amino sugars linked to an aminocyclitol ring by glycosidic bonds. They have similar mechanisms of action and properties, but differ somewhat in spectrum of action, toxicity, and susceptibility to bacterial resistance. The compounds are bactericidal, with activity against both gram-positive and gram-negative organisms, and act by binding to proteins on the 30S ribosome of bacteria and inhibiting protein synthesis. The aminoglycosides also bind to isolated LPS and have a very weak outer membrane permeabilizing effect. [Taber et al., *Microbiological Reviews* 53: 439–457 (1987)); Kadurugamuwa et al., *Antimicrobial Agents and Chemotherapy*, 37: 715–721 (1993); Vaara, *Microbiological Reviews* 56: 395–411 (1992)]. This class of antibiotics includes amikacin, gentamicin, kanamycin, neomycin, netilmycin, paromomycin or tobramycin. The aminoglycosides are usually reserved for more serious infections because of severe adverse effects including ototoxicity and nephrotoxicity. There is a narrow therapeutic window between the concentration required to produce a therapeutic effect, e.g., 8 $\mu$g/ml for gentamicin, and the concentration that produces a toxic effect, e.g., 12 $\mu$g/ml for gentamicin. Neomycin in particular is highly toxic and is never administered parenterally.

Tetracyclines have a common four-ring structure and are closely congeneric derivatives of the polycyclic naphthacenecarboxamide. The compounds are bacteriostatic, and inhibit protein synthesis by binding to the 30S subunit of microbial ribosomes and interfering with attachment of aminoacyl tRNA. The compounds have some activity against both gram-positive and gram-negative bacteria; however, their use is limited because many species are now relatively resistant. Adverse effects include gastrointestinal effects, hepatotoxicity with large doses, and nephrotoxicity in some patients. This antibiotic class includes tetracycline, chlortetracycline, demeclocycline, doxycycline, methacycline, minocycline or oxytetracycline.

The sulfonamides are derivatives of sulfanilamide, a compound similar in structure to para-aminobenzoic acid (PABA), which is an essential precursor for bacteria synthesis of folic acid. The compounds are generally bacteriostatic, and act by competitively inhibiting incorporation of PABA into tetrahydrofolic acid, which is a required cofactor in the synthesis of thymidines, purines and DNA. Sulfonamides have a wide range of activity against gram-positive and gram-negative bacteria, but their usefulness has diminished with increasingly high prevalence of bacterial resistance. The sulfonamide class of antibiotics includes sulfacytine, sulfadiazine, sulfamethizole, sulfisoxazole, sulfamethoxazole, sulfabenzamide or sulfacetamide. Adverse effects include hypersensitivity reactions and occasional hematological toxicity.

Trimethoprim is an inhibitor of the dihydrofolate reductase enzyme, which converts dihydrofolic to tetrahydrofolic acid, a required factor for DNA synthesis. Adverse effects include gastrointestinal distress and rare hematological toxicity. Trimethoprim is also available in combination with sulfamethoxazole (also known as co-trimoxazole). The combination is usually bactericidal, although each agent singly is usually bacteriostatic. The combination is the drug of choice for Salmonella infections, some Shigella infections, *E. coli* traveler's diarrhea and *Pneumocystis carinii* pneumonia.

The fluoroquinolones and quinolones are derivatives of nalidixic acid, a naphthyridine derivative. These compounds are bactericidal, and impair DNA replication, transcription and repair by binding to the DNA and interfering with DNA gyrase, an enzyme which catalyzes negative supercoiling of DNA. The fluoroquinolones, which include norfloxacin, ciprofloxacin, or ofloxacin, and the quinolones, which include cinoxacin, have a broad spectrum of antimicrobial activity against gram-negative and gram-positive organisms. These compounds distribute widely through extravascular tissue sites, have a long serum half-life, and present few adverse effects. Because of their effect on DNA, the drugs are contraindicated in pregnant patients and in children whose skeletal growth is incomplete.

Vancomycin is a glycopeptide, with a molecular weight of about 1500, produced by a fungus. It is primarily active against gram-positive bacteria. The drug inhibits one of the final steps in synthesis of the bacterial cell wall, and is thus effective only against growing organisms. It is used to treat serious infections due to gram-positive cocci when penicillin G is not useful because of bacterial resistance or patient allergies. Vancomycin has two major adverse effects, ototoxicity and nephrotoxicity. These toxicities can be potentiated by concurrent administration of another drug with the same adverse effect, such as an aminoglycoside.

The macrolides are bacteriostatic and act by binding to the 50S subunit of 70S ribosomes, resulting in inhibition of protein synthesis. They have a broad spectrum of activity against gram-positive and gram-negative bacteria and may be bacteriostatic or bactericidal, depending on the concentration achieved at sites of infection. The compounds distribute widely in body fluids. Adverse effects include gastrointestinal distress and rare hypersensitivity reactions. The most common macrolide used is erythromycin, but the class includes other compounds such as clarithromycin or azithromycin.

The polymyxins are a group of closely related antibiotic substances produced by strains of *Bacillus polymyxa*. These drugs, which are cationic detergents, are relatively simple, basic peptides with molecular weights of about 1000. Their antimicrobial activity is restricted to gram-negative bacteria. They interact strongly with phospholipids and act by penetrating into and disrupting the structure of cell membranes. Polymyxin B also binds to the lipid A portion of endotoxin and neutralizes the toxic effects of this molecule. Polymyxin B has severe adverse effects, including nephrotoxicity and neurotoxicity, and should not be administered concurrently with other nephrotoxic or neurotoxic drugs. The drug thus has limited use as a therapeutic agent because of high systemic toxicity, but may be used for severe infections, such as *Pseudomonas aeruginosa* meningitis, that respond poorly to other antibiotics.

Chloramphenicol inhibits protein synthesis by binding to the 50S ribosomal subunit and preventing binding of aminoacyl tRNA. It has a fairly wide spectrum of antimicrobial activity, but is only reserved for serious infections, such as meningitis, typhus, typhoid fever, and Rocky Mountain spotted fever, because of its severe and fatal adverse hematological effects. It is primarily bacteriostatic, although it may be bactericidal to certain species.

Lincomycin and clindamycin are lincosamide antimicrobials. They consist of an amino acid linked to an amino sugar. Both inhibit protein synthesis by binding to the 50S ribosomal subunit. They compete with erythromycin and chloramphenicol for the same binding site but in an overlapping fashion. They may be bacteriostatic or bactericidal, depending on relative concentration and susceptibility. Gastrointestinal distress is the most common side effect. Other adverse reactions include cutaneous hypersensitivity, transient hematological abnormalities, and minor elevations of hepatic enzymes. Clindamycin is often the drug of choice for infections caused by anaerobic bacteria or mixed aerobic/anaerobic infections, and can also be used for susceptible aerobic gram-positive cocci.

Some drugs, e.g. aminoglycosides, have a small therapeutic window. For example, 2 to 4 $\mu$g/ml of gentamicin or tobramycin may be required for inhibition of bacterial growth, but peak concentrations in plasma above 6 to 10 µg/ml may result in ototoxicity or nephrotoxicity. These agents are more difficult to administer because the ratio of toxic to therapeutic concentrations is very low. Antimicrobial agents that have toxic effects on the kidneys and that are also eliminated primarily by the kidneys, such as the aminoglycosides or vancomycin, require particular caution because reduced elimination can lead to increased plasma concentrations, which in turn may cause increased toxicity. Doses of antimicrobial agents that are eliminated by the kidneys must be reduced in patients with impaired renal function. Similarly, dosages of drugs that are metabolized or excreted by the liver, such as erythromycin, chloramphenicol, or clindamycin, must be reduced in patients with decreased hepatic function.

Bacteria acquire resistance to antibiotics through several mechanisms: (1) production of enzymes that destroy or inactivate the antibiotic [Davies, *Science*, 264:375–381 (1994)]; (2) synthesis of new or altered target sites on or within the cell that are not recognized by the antibiotic [Spratt, *Science*, 264:388–393 (1994)]; (3) low permeability to antibiotics, which can be reduced even further by altering cell wall proteins, thus restricting access of antibiotics to the bacterial cytoplasmic machinery; (4) reduced intracellular transport of the drug; and (5) increased removal of antibiotics from the cell via membrane-associated pumps [Nikaido, *Science*, 264:382–387 (1994)].

The susceptibility of a bacterial species to an antibiotic is generally determined by any art recognized microbiological method. A rapid but crude procedure uses commercially available filter paper disks that have been impregnated with a specific quantity of the antibiotic drug. These disks are placed on the surface of agar plates that have been streaked with a culture of the organism being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration.

The resistance or susceptibility of an organism to an antibiotic is determined on the basis of clinical outcome, i.e., whether administration of that antibiotic to a subject infected by that organism will successfully cure the subject. While an organism may literally be susceptible to a high concentration of an antibiotic in vitro, the organism may in fact be resistant to that antibiotic at physiologically realistic concentrations. If the concentration of drug required to inhibit growth of or kill the organism is greater than the concentration that can safely be achieved without toxicity to the subject, the microorganism is considered to be resistant to the antibiotic. To facilitate the identification of antibiotic resistance or susceptibility using in vitro test results, the National Committee for Clinical Laboratory Standards (NCCLS) has formulated standards for antibiotic susceptibility that correlate clinical outcome to in vitro determinations of the minimum inhibitory concentration of antibiotic.

As used herein, "BPI protein product" includes naturally or recombinantly produced BPI protein; natural, synthetic, or recombinant biologically active polypeptide fragments of BPI protein; biologically active polypeptide variants of BPI protein or fragments thereof, including hybrid fusion proteins or dimers; biologically active polypeptide analogs of BPI protein or fragments or variants thereof, including cysteine-substituted analogs; or BPI-derived peptides. The BPI protein products administered according to this invention may be generated and/or isolated by any means known in the art. U.S. Pat. Nos. 5,198,541 and 5,641,874, the disclosures of which are incorporated herein by reference, disclose recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein, including those described in U.S. Pat. Nos. 5,198,541 and 5,641,874. Non-limiting examples of such fragments include an N-terninal fragment of natural human BPI of approximately 25 kD, described in Ooi et al., *J. Exp. Med.*, 174:649 (1991), or the recombinant expression product of DNA encoding N-terminal amino acids from 1 to about 193 to 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for rBPI$_{23}$ and with the exception that residue 417 is alanine (specified by GCT) rather than valine (specified by GTT). Another fragment consisting of residues 10–193 of BPI has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI fragments, as described in U.S. Pat. Nos. 5,447,913, 5,703,038, and 5,856,302 and corresponding International Publication No. WO 95/24209 (PCT/US95/03125), all of which are incorporated herein by reference.

Biologically active variants of BPI (BPI variants) include but are not limited to recombinant hybrid fusion proteins, comprising BPI holoprotein or biologically active fragment thereof and at least a portion of at least one other polypeptide, or dimeric forms of BPI variants. Examples of such hybrid fusion proteins and dimeric forms are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. Nos. 5,420,019, 5,674, 834 and 5,827,816 and corresponding International Publication No. WO 94/18323 (PCT/US94/01235), all of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}$Δcys or rBPI21. Production of this N-terminal analog of BPI, rBPI$_{21}$, has been described in Horwitz et al., *Protein Expression Purification*, 8:28–40 (1996). Similarly, an analog consisting of residues 10–193 of BPI in which the cysteine at position 132 is replaced with an alanine (designated "rBPI(10–193)C132A" or "rBPI(10–193) ala$^{132}$") has been described in U.S. Pat. No. 6,013,631, continuation-in-part U.S. application Ser. No.09/336,402, filed Jun. 18, 1999, and corresponding International Publication No. WO 99/66044 (PCT/US99/13860), all of which are incorporated herein by reference. Other examples include dimeric forms of BPI analogs; e.g. U.S. Pat. Nos. 5,447,913, 5,703,038, and 5,856,302 and corresponding International Publication No. WO 95/24209 (PCT/US95/ 03125), all of which are incorporated herein by reference.

Other BPI protein products useful according to the methods of the invention are peptides derived from or based on BPI produced by synthetic or recombinant means (BPI-derived peptides), such as those described in International Publication No. WO 97/04008 (PCT/US96/03845), which corresponds to U.S. application Ser. No. 08/621,259 filed Mar. 21, 1996, and International Publication No. WO 96/08509 (PCT/US95/09262), which corresponds to U.S. Pat. No. 5,858,974, and International Publication No. WO 95/19372 (PCT/US94/10427), which corresponds to U.S. Pat. Nos. 5,652,332 and 5,856,438, and International Publication No. WO94/20532 (PCT/US94/02465), which corresponds to U.S. Pat. No. 5,763,567 which is a continuation of U.S. Pat. No. 5,733,872, which is a continuation-in-part of U.S. application Ser. No. 08/183,222, filed Jan. 14, 1994, which is a continuation-in-part of U.S. application Ser. No. 08/093,202 filed Jul. 15, 1993 (corresponding to International Publication No. WO 94/20128 (PCT/US94/02401)), which is a continuation-in-part of U.S. Pat. No. 5,348,942, as well as International Application No. PCT/US97/05287, which corresponds to U.S. Pat. No. 5,851,802, the disclosures of all of which are incorporated herein by reference. Methods of recombinant peptide production are described in U.S. Pat. No. 5,851,802 and International Publication No. WO 97/35009 (PCT/US97/05287), the disclosures of which are incorporated herein by reference.

Exemplary BPI protein products include recombinantly-produced N-terminal analogs or fragments of BPI, especially those having a molecular weight of approximately between 20 to 25 kD such as rBPI$_{21}$, rBPI$_{23}$, rBPI(10–193) C132A, (rBPI(10–193)ala$^{132}$), dimeric forms of these N-terminal polypeptides (e.g., rBPI$_{42}$ dimer), or BPI-derived peptides. Exemplary BPI-derived peptides include XMP.391 (SEQ ID NO: 4), XMP.416 (SEQ ID NO: 5) or XMP.445 (SEQ ID NO: 6) [the structure and activity of which are described in co-owned, co-pending U.S. Ser. No. U.S. Ser. No. 09/406,243 filed Sep. 24, 1999, incorporated herein by reference].

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., rBPI$_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., rBPI$_{21}$,) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034, 5,696,090 and 5,955,427 and corresponding International Publication No. WO 94/17819 (PCT/US94/01239), the disclosures of all of which are incorporated herein by reference. As described in U.S. Pat. No. 5,912,228 and corresponding International Publication No. WO96/21436 (PCT/US96/01095), all of which are incorporated herein by reference, other poloxamer formulations of BPI protein products with enhanced activity may be utilized, optionally with EDTA.

A further aspect of the invention provides methods for the rational design of molecules that function like antimicrobial BPI protein products. For example, peptides or other organic molecules may be synthesized that mimic the structure and function of BPI-derived peptides with antibacterial activity. The molecules thus designed may be screened according to any of the assays described above. Methods of treating infection using such molecules are also contemplated.

Yet a further aspect of the invention provides methods for identifying compounds that alone exhibit no antimicrobial activity, e.g., due to insufficient ability to penetrate the target cell wall or membrane, but that act as antimicrobial compounds when administered in conjunction with BPI-derived peptides. These compounds are identified by screening them in combination with BPI-derived peptides according to any of the assays described above.

The discovery that BPI protein products also inhibit mammalian mitochondrial ATPase activity provides a basis for use of these compounds, particularly BPI-derived peptides as anti-proliferative or cytotoxic agents that can be used to treat conditions for which an inhibition of cellular proliferation is desirable. BPI protein products may be administered for this purpose in conjunction with targeting and/or penetrating agents that target delivery to specific desired cells and allow penetration of the BPI protein product to the interior of the cell so that it can act on the mammalian mitochondrial ATP synthase. Suitable targeting agents include antibodies, binding proteins (including receptors or ligands) or fragments thereof that specifically or preferentially react with the target cells, and can be associated with the BPI-derived peptides in a covalent manner via chemical conjugation or in a non-covalent manner, e.g., through liposomes.

Conditions that may benefit from administration of anti-proliferative or cytotoxic agents include cancer or other neoplastic diseases (e.g., solid tumors/malignancies, locally advanced tumors, metastatic cancer, blood cell malignancies, lymphomas, lung cancer, breast cancer, gastrointestinal cancers, including stomach cancer, colon cancer or colorectal cancer, pancreatic cancer, liver cancer, urological cancers, malignancies of the female genital tract, including ovarian cancer, endometrial cancer, kidney cancer, brain cancer, bone cancers, skin cancers, including malignant melanoma, or Kaposi's sarcoma); autoimmune diseases (e.g., rheumatoid arthritis, psoriasis, scleroderma or systemic lupus erythematosus), ectopic pregnancy, endometriosis, warts, etc.

Other aspects and advantages of the present invention will be understood upon consideration of the following illustrative examples. Example 1 addresses the testing of an antibacterial BPI protein product compounds for inhibition of the activity of bacterial ATP synthase, as measured by oxygen consumption. Example 2 addresses the testing of antibacterial BPI protein product compounds for inhibition of the activity of bacterial ATP synthase, as measured by a metabolic indicator dye and a membrane potential indicator dye. Example 3 addresses testing of antibacterial BPI protein products for inhibition of the activity of bacterial ATP synthase, as measured by phosphatase activity (Example 3A) and synthase activity (Example 3B). Example 4 addresses the testing of antimicrobial compounds for in vitro effect on target cells. Example 5 addresses testing of BPI protein products for inhibition of mammalian mitochondrial ATP synthesis activity. Example 6 addresses testing of candidate compounds for effect on uncoupling electron transport from ATP synthesis.

EXAMPLE 1
Effect of Antibacterial Compounds on Bacterial Oxygen Consumption

The effect of antibacterial BPI protein product rBPI$_{21}$ on the activity of bacterial ATP synthase as measured by oxygen consumption was determined as follows. *E. coli* J5 bacteria were grown overnight in TSB [DIFCO Labs]. The bacteria were then diluted at a ratio of 1:20 and allowed to grow for 3 hours to reach mid log growth, an approximate concentration of 1×10$^7$ cells/mL. 1 mL of media was placed in a tube and the dissolved O$_2$ content was measured with a Lazar Research Laboratories Micro pO2 System (Los Angeles, Calif.). Either rBPI$_{21}$ (to a final concentration of 32 µg/mL) or control was added to the tubes, followed by 50 µL of the bacterial suspension in each tube. The O$_2$ content was determined over time by measuring the voltage reading of the oxygen meter. The results are displayed in FIG. 1, in which 0.1 m Volt is equal to 1 ppm dissolved O$_2$ and the rate of change in O$_2$ content indicates the amount of O$_2$ utilization. The steepness of the downward curve in FIG. 1 shortly after addition of the bacteria and rBPI$_{21}$ indicates that there was an apparent increase in oxygen uptake, and is consistent with an inhibition of bacterial ATP synthase activity.

Although previous reports described decreased oxygen consumption in BPI-treated bacteria, those results may have been due to the use of higher concentrations of BPI that are more potently bactericidal. It is possible that the apparent increased oxygen consumption observed in this experiment is best observed at a concentration less than the minimum bactericidal concentration.

Alternatively, a Clark-type oxygen electrode may be used (Hansatech Oxygraph, Cole-Parmer, Vernon Hills, Ill.). *E. coli* J5 cells in mid log growth are diluted into TSB (prewarmed to 37° C.) to a final concentration of 8×10$^7$ cells/mL. 1 mL aliquots are removed every 5 minutes and placed into the oxygen electrode to assess oxygen utilization rate. The bacterial culture is monitored for 45 minutes and compared to a control culture without added test compound. Over longer time frames such as these, the oxygen utilization rate of the cells is observed to decrease, presumably due to the bactericidal effect of the test compound.

EXAMPLE 2
Effect of Antibacterial Compounds on Apparent Metabolic Activity

The effect of antibacterial BPI protein products on the activity of bacterial ATP synthase as measured by a metabolic oxidation-reduction indicator dye and a membrane potential indicator dye was determined as described in Example 2 of U.S. Provisional Application Ser. No. 60/143, 290 filed Jul. 12, 1999 and corresponding co-owned, concurrently filed U.S. application Ser. No. 09/543,955, both of which are incorporated herein by reference and Example 9 of U.S. Provisional Application Ser. No. 60/143,485 filed Jul. 12, 1999 and corresponding U.S. application Ser. No. 09/404,926 filed Sep. 24, 1999 and International Application No. PCT/US99/22361 filed Sep. 24, 1999, all of which are incorporated herein by reference.

The results of experiments with metabolic indicator dye Alamar Blue™ showed that treatment of *E. coli* with the antibacterial BPI protein products rBPI$_{21}$, XMP.365 (SEQ ID NO: 3) [structure described in U.S. Pat. No. 5,858,974] and XMP.391 (SEQ ID NO: 4) produced an apparent increased metabolic activity relative to untreated controls.

The results of experiments with membrane potential indicator dye DiOC$_6$(3) showed that treatment of *E. coli* J5 with rBPI$_{21}$ (which has in vitro bactericidal activity against this strain) produced an accumulation and retention of the dye despite cell death, while treatment of *E. coli* O111:B4 with rBPI$_{21}$ (which does not have in vitro bactericidal activity against this strain) did not produce an accumulation and retention of the dye. The results of further experiments with DiOC$_6$(3) showed that treatment of *E. coli* O111:B4 with XMP.365 [SEQ ID NO: 3] (which has in vitro bactericidal activity against this strain) produced an accumulation and retention of the dye despite cell death.

EXAMPLE 3
Effect of Antibacterial Compounds on Enzymic Activity of Bacterial ATP Synthase Example 3A
Effect on Phosphatase Activity The effect of antibacterial BPI protein products on the phosphatase activity of an *E. coli* ATP synthase was determined as follows. For bacterial ATP synthase preparations, bacterial cells were first grown overnight in TSB [Difco Labs]. They were then pelleted by spinning at 3500 rpm for 5 minutes and washed twice with ddH$_2$O. Cells were resuspended in 30 mM Tris-HCl, pH 7.4, 10 mM EDTA, pH 7.4, 0.5 mg/mL lysozyme [SIGMA, St. Louis, Mo.] and left at room temperature for 30 minutes to spheroplast the cells. Cells were then pelleted and lysed with 1% SDS by mixing by inversion and leaving on ice for 5 minutes. The membranes were collected by ultracentrifugation at 150,000×g for 1.5 hours. Membranes were washed twice with 50 mM Tris-HCl, pH 7.5, 5 mM MgSO$_4$, 1 mM dithiotlreitol, 1 mM PMSF, 10% glycerol (w/v) at 4 degrees. Membranes were resuspended in incubation buffer (10 mM MES-Tris, pH 6.5, 25 mM NH$_4$Cl) and assayed for ATPase activity.

The effect of test compounds (XMP.391 [SEQ ID NO: 4] and rBPI$_{21}$ at final concentrations ranging from 40 µg/mL to 1.25 µg/mL, and azide at final concentrations ranging from 1.25 mM to 0.039 mM) on the enzymic activity of the ATPase in the suspensions was measured by the colorimetric determination of phosphate release, as follows. Assays were conducted in a 96-well plate. Each well contained approximately 10–15 µL (per 100 µL total volume) mitochondrial suspension/microsome suspension in incubation buffer (10 mM MES-Tris, pH 6.5, 25 mM NH$_4$Cl). Five µL of various dilutions of a test compound were added. Each plate contained an Enzyme Blank [test compound and buffer alone, without the ATPase-containing suspension], a Positive Control [ATPase-containing suspension alone, without test compound added], and a Phosphate Standard [ATPase-containing suspension containing 50 nM phosphate (5 µl of 10 mM $NaH_2PO_4$)].

The 96-well plate was incubated 10 min at 21° C. (room temperature). The reaction was initiated by adding 50 µl of ATP Stock solution [10 mM MES, 15 mM ATP, 15 mM $MgSO_4$, 25 mM $NH_4Cl$, 0.05% (w/v) deoxycholate, adjusted to pH 6.5 with Tris base] to each well. The plate was incubated for a total of 15 minutes. Plates were centrifuged in a Beckman J-6M centrifuge for 5 minutes at 1200 rpm. One hundred µL of each supernatant was transferred to a new 96-well plate. One hundred µl of Color Developing Reagent, a combined stop solution and color development reagent, was added [prepared by adding 0.5 g Ascorbic acid to 30 ml $H_2O$, followed by adding 5 ml 12% Ammonium Molybdate in 12N $H_2SO_4$ and 5 ml of 10% sodium lauryl sulfate, followed by adjusting total volume to 50 ml with $H_2O$]. All reagents were added to each row at 30 second intervals to ensure that all samples are incubated for the identical length of time. The $OD_{650nm}$ of each well was determined using a Molecular Devices Vmax Kinetic Microplate Reader (Sunnyvale, Calif.), and the OD value for the Enzyme Blank was subtracted from each value.

Results showed that XMP.391 (SEQ ID NO: 4) and azide inhibited phosphatase activity of bacterial membrane preparations in a dose-dependent manner at concentrations of about 10 µg/mL and higher.

U.S. Provisional Application Ser. No. 60/143,372 filed Jul. 12, 1999 and corresponding co-owned, concurrently filed U.S. application Ser. No. 09/543,802, both of which are incorporated herein by reference, demonstrates that antifungal BPI protein products inhibit fungal mitochondrial ATP synthase activity.

Example 3B
Effect on ATP Synthesis Activity

The effect of antibacterial BPI protein products on the ATP synthesis activity of an *E. coli* ATP synthase was determined as follows. Bacterial membranes were prepared as follows. A 400 mL culture of *E. coli* was grown overnight in TSB at 37° C. with shaking. Cells were harvested by centrifugation for 10 minutes at 1000×g, followed by washing with 20 mL of PBS and recentrifugation. Cells were resuspended in 4 ml of 25 mM HEPES, pH 7.6, 0.1 M KCl, 0.1 M EDTA, 12.5 mM $MgCl_2$, 10% glycerol, 0.1% NP40. Then 50 µl of lysozyme (50 mg/ml) was added and the cells were incubated for 30 minutes on ice. Cells were disrupted by sonication in 3×30-second pulses. Cells were placed on ice between pulses. DNAse I was added to a 10 µg/mL final concentration (GIBCO Life Technologies, Gaithersburg, Md.) and the homogenate was left on ice for 30 minutes. The suspension was then centrifuged at 12,000×g for 30 minutes at 4° C. The pellet was resuspended in 8 ml of 10 mM Tris, pH 7.0, 0.1 mM EDTA, 20% glycerol. The suspension was loaded on top of a sucrose step gradient with three steps as follows: 8 mL 2.25 M sucrose, 8 mL 1.65 M sucrose, 8 mL 1.1 M sucrose. The gradients were centrifuged overnight at 20,000×g. The membrane band was collected the next day and diluted with 4 volumes of $ddH_2O$ and recentrifuged at 12,000×g for 30 minutes. The final pellet was resuspended in 2 mL 10 mM Tris-HCl, pH 7.0, 0.1 mM EDTA, 20% glycerol and protein concentration was determined by standard Bradford assay. This resulting bacterial membrane preparation is capable of synthesizing ATP when given ADP.

ATP synthesis activity was measured using an adaptation of Fillingame et al., *J. Biol. Chem.*, 266(31):20934–20939 (1991). In a 96 well plate (Microlite 1, DYNEX Technologies, Chantilly Va.), 25 µg bacterial membranes were diluted into 100 µl of 55.5 mM Tris-HCl, pH 7.8, 0.222 mM $MgSO_4$ plus the compound to be tested (XMP.391 (SEQ ID NO: 4) and rBPI21 at concentrations ranging from 40 µg/mL to 0.625 µg/mL). This mixture was incubated for 20 minutes at 30° C. with shaking. An aliquot of 50 µl of ADP in the above buffer was then added to a final concentration of 1 MM and the mixture was incubated for another 20 minutes at room temperature. 100 µl of luciferin/luciferase ATP assay mixture (Molecular Probes ATP Determination Kit, Eugene, Oreg.) was added and the plate was immediately assayed for chemiluminescence using a 96-well fluorimeter (SpectraMAX Gemini, Molecular Devices, Sunnyvale, Calif.). Assays were read in Endpoint mode with 30 reads per well.

Results showed that XMP.391 (SEQ ID NO: 4) inhibited the synthesis of ATP from ADP in the bacterial membrane preparations in a dose-dependent manner at concentrations of about 1 µg/mL and higher.

EXAMPLE 4
Testing of Antimicrobial Compounds For In Vitro or In Vivo Effect on Organisms Antimicrobial compounds are tested for in vitro effect on organisms according to any procedures known in the art, including those described in U.S. Pat. Nos. 5,523,288, 5,578,572, 5,627,153, 5,858,974 and 5,646,114, all of which are incorporated herein by reference.

EXAMPLE 5
Effect of Test Compounds on Mammalian Mitochondrial ATP Synthase Activity The effect of BPI protein products on ATP synthase enzymic activity in mitochondrial preparations was evaluated. Mitochondrial membrane preparations were prepared as follows. Male laboratory mice (Mus musculus) were sacrificed by cervical dislocation and their livers were immediately excised. The gall bladder and connective tissues were removed and the livers were washed in 0.25 M sucrose. Wet liver weight was determined after blotting the washed liver on absorbent paper. All subsequent steps of the fractionation procedure were performed on ice. The weighted livers were then homogenized with a Potter Elvehjem tissue homogenizer and six passes of a teflon pestle in 9 volumes of 0.25 M sucrose with protease inhibitors (2 µg/mL pepstatin A, 2 µg/mL aprotinin and 1 mM phenylmethylsulfonyl fluoride (PMSF). Liver homogenates were then centrifuged in a Beckman (Fullerton, Calif.) J2-21 centrifuge for 10 minutes at 600×g. The 600×g pellet (nuclei, unbroken cells and connective tissue) was discarded and the supernatant was subjected to further centrifugation. The 600×g supernatant was centrifuged at 7000×g for 10 minutes to yield a crude mitochondrial pellet.

Crude mitochondria were resuspended in 3 volumes of the original liver weight with 0.25 M sucrose and centrifuged at 7000×g for 10 minutes. The supernatant was discarded and the procedure was repeated. Washed mitochondria were resuspended in 0.25 M sucrose to a volume equivalent to the original wet liver weight. Complete lysis was accomplished with 0.2% sodium deoxycholate for 20 minutes. Mitochondria were pelleted by centrifugation at 40000×g for 20 minutes. The pellet was resuspended in 0.25 M sucrose with protease inhibitors at a volume equal to the original wet liver weight.

The effect of various test compounds on the enzymic activity of the ATPase in the suspension was measured by the colorimetric determination of phosphate release, as follows. Assays were conducted in a 96-well plate. Each well contained approximately 10–15 μL (per 100 μL total volume) mitochondrial suspension/microsome suspension in incubation buffer (10 mM MES-Tris, pH 6.5, 25 mM NH$_4$Cl). Five μL of one of the following test compounds were added to give the indicated final concentration: 1.35 μM rBPI$_{21}$, 0.37 μM omeprazole acid, 0.37 μM omeprazole, 0.25 μM oligomycin, 10 mg/ml efrapeptin F&G, 0.015 μM sodium azide, 0.076 μM XMP.416 (SEQ ID NO: 5), 0.082 μM XMP.391 (SEQ ID NO: 4), 0.553 μM XMP.416 and 0.482 μM XMP.391. Each plate contained an Enzyme Blank [test compound and buffer alone, without the ATPase-containing suspension], a Positive Control [ATPase-containing suspension alone, without test compound added], and a Phosphate Standard [ATPase-containing suspension containing 50 nM phosphate (5 μl of 10 mM NaH$_2$PO$_4$)].

The 96-well plate was incubated 10 min at 21° C. (room temperature). The reaction was initiated by adding 50 μl of ATP Stock solution [10 mM MES, 15 mM ATP, 15 mM MgSO$_4$, 25 mM NH$_4$Cl, 0.05% (w/v) deoxycholate, adjusted to pH 6.5 with Tris base] to each well. The plate was incubated for a total of 15 minutes. Plates were centrifuged in a Beckman J-6M centrifuge for 5 minutes at 1200 rpm. One hundred μL of each supernatant was transferred to a new 96-well plate. One hundred μl of Color Developing Reagent, a combined stop solution and color development reagent, was added [prepared by adding 0.5 g Ascorbic acid to 30 ml H$_2$O, followed by adding 5 ml 12% Ammonium Molybdate in 12N H$_2$SO$_4$ and 5 ml of 10% sodium lauryl sulfate, followed by adjusting total volume to 50 ml with H$_2$O]. All reagents were added to each row at 30 second intervals to ensure that all samples were incubated for the identical length of time. The OD$_{650nm}$, of each well was determined using a Molecular Devices Vmax Kinetic Microplate Reader (Sunnyvale, Calif.), and the OD value for the Enzyme Blank was subtracted from each value.

Results showed that all of the BPI protein products tested (rBPI$_{21}$, XMP.391 and XMP.416) inhibited the phosphatase activity of ATP synthase in the mitochondrial membrane preparations.

The effect of test compounds on mammalian mitochondrial preparations can also be tested by evaluating oxygen consumption as follows. A Clark-type oxygen electrode may be used (Hansatech Oxygraph, Cole-Parmer, Vernon Hills, Ill.). The oxygen electrode buffer is 10 mM Tris-HCl, pH 6.5, 0.65 M sorbitol, 0.36 mM EDTA, 10 mM KH$_2$PO$_4$, 10 mM KCl, 0.3% BSA. Mitochondria are added to a final concentration of 1–2 mg/mL. A substrate (succinate) is added to a 5 mM final concentration, and the oxygen consumption rate (state 3) is measured. Then ADP is added in pulses to a final concentration of 2.5 mM, and the oxygen utilization rate (state 4) is measured. Test compounds are added after an initial testing of State 3 and State 4 respiration, and then ADP is added to test the effect on both State 3 and State 4. State 3 respiration refers to respiration where all necessary components (ADP, substrate) are in excess, and respiration is at the maximal coupled rate. State 4 respiration occurs following State 3 when ADP is depleted. Uncoupled respiration occurs when ATP synthase is uncoupled from electron transport, and thus oxygen utilization is at the maximal rate. [See, e.g., Estabrook, *Methods Enzymol.*, 52:43–47 (1978)].

EXAMPLE 6

Effect of Test Compounds on Uncoupling Electron Transport

Uncoupling agents act to uncouple electron transport from ATP synthesis. The ability of a potential compound to act as an uncoupling agent can be evaluated in any way known in the art, including by measuring oxygen uptake of, e.g., mitochondria, bacterial spheroplasts (missing a cell wall), or permeabilized whole cells using an oxygen electrode as described above in Examples 1 and 5, and optionally combined with an ATP synthesis activity assay, e.g., as described in Example 3B above. Whole cells (e.g. bacteria) or mitochondria from eukaryotic including mammalian cells may be isolated as previously described. After coupled and controlled oxygen utilization has been observed (i.e., oxygen consumption dependent upon ADP and added substrate), the candidate compound is added to the chamber in varying concentrations and the rate of oxygen consumption is measured. The maximally effective uncoupling concentration of the test compound is selected (i.e., the concentration that achieves the maximum rate of oxygen consumption in the presence of excess substrate without increasing ATP synthesis) and the rate of oxygen consumption is measured in the presence of this concentration of test compound. Next, a known uncoupling agent is added at its maximally effective uncoupling concentration and oxygen utilization is observed. If there is no increase in respiration rate upon addition of the known uncoupling agent, then the compound can be considered an electron uncoupler. Any uncoupling agents known in the art can be used, including carbonylcyanide p-trifluoromethoxyphenylhdrazone (FCCP, Sigma, St. Louis Mo.), e.g., at a final concentration of 0.2 μM [see Westerhoff et al., *Proc. Nat'l. Acad. Sci. USA* 86:6597–6601 (1989)], dinitrophenyl (DNP, Sigma), e.g., at a final concentration of 20 μg/mL, or carbonylcyanide m-chlorohydrazone (CCCP, Sigma), e.g., at a final concentration of 1 μM [see Hugosson et al., *Eur. J. Biochem.* 223:1027–1033 (1994)].

Numerous modifications and variations of the above-described invention are expected to occur to those of skill in the art. Accordingly, only such limitations as appear in the appended claims should be placed thereon.

What is claimed are:

1. A method of identifying a candidate antimicrobial compound comprising the steps of:
   (a) selecting a test compound that produces a decrease in the activity of an $F_1/F_0$ ATP synthase; and
   (b) detecting inhibition of growth of microbial target cells in the presence of the selected test compound from step (a).

2. The method of claim 1 further comprising the step (c) of detecting growth of a non-target cell in the presence of the selected test compound from step (a), concurrently with or separately from step (b).

3. A method of identifying a candidate antibacterial compound comprising the steps of:
   (a) selecting a test compound that produces a decrease in the activity of an $F_1/F_0$ ATP synthase; and
   (b) detecting inhibition of growth of bacterial cells in the presence of the selected test compound from step (a).

4. The method of claim 3 further comprising the step (c) of detecting growth of a non-bacterial cell in the presence of the selected test compound from step (a), concurrently with or separately from step (b).

5. The method of claim 1 or 3 wherein step (a) comprises measuring phosphatase activity of the $F_1/F_0$ ATP synthase.

6. The method of claim 1 or 3 wherein step (a) comprises measuring ATP synthesis activity of the $F_1/F_0$ ATP synthase.

7. The method of claim 1 wherein step (a) comprises measuring oxygen consumption of a mitochondria comprising the $F_1/F_0$ ATP synthase.

8. The method of claim 7 wherein step (a) further comprises measuring oxygen consumption by the mitochondria in the presence of an uncoupling agent.

9. The method of claim 3 wherein step (a) comprises measuring oxygen consumption of a bacterial cell or membrane preparation.

10. The method of claim 9 wherein step (a) further comprises measuring oxygen consumption of the bacterial cell or membrane preparation in the presence of an uncoupling agent.

11. The method of claim 1 or 3 wherein step (a) comprises measuring metabolic activity of a microbial cell comprising the $F_1/F_0$ ATP synthase.

12. The method of claim 11 wherein the metabolic activity is measured using a tetrazolium dye.

13. The method of claim 2 or 4 wherein in step (c) growth of mammalian cells is detected.

14. The method of claim 13 wherein a test compound that produces a greater inhibition of microbial target cell growth relative to mammalian cell growth is selected.

15. A method of identifying a candidate antimicrobial compound comprising the steps of:
   (a) selecting a test compound that produces a decrease in the activity of an $F_1/F_0$ ATP synthase; and
   (b) detecting a reduction in total ATP levels of a microbial target cell in the presence of the selected test compound.

16. The method of claim 15 further comprising the step of:
   detecting inhibition of growth of microbial target cells in the presence of the selected test compound.

17. A method of identifying a candidate antimicrobial compound comprising the steps of:
   (a) selecting a test compound that interacts with an $F_1/F_0$ ATP synthase; and
   (b) detecting inhibition of growth of microbial target cells in the presence of the selected test compound from step (a).

18. The method of any one of claims 15 through 17 further comprising the step of:
   detecting growth of a non-target cell in the presence of the selected test compound.

19. The method of claim 18 wherein the non-target cell is a mammnalian cell and wherein a test compound that produces a greater inhibition of microbial target cell growth relative to mammalian cell growth is selected.

20. A method of identifying an antimicrobial compound comprising the steps of:
   (a) determining the oxygen consumption of microbial target cell or component thereof in the presence of a test compound at a maximally effective uncoupling concentration;
   (b) determining oxygen consumption of the microbial target cell or component thereof after further addition of an uncoupling agent at a maximally effective uncoupling concentration,
   (c) selecting a test compound for which there is no significant increase in oxygen consumption determined in step (b) compared to step (a); and
   (d) detecting inhibition of growth of microbial target cells in the presence of the selected test compound from step (b).

21. The method of claim 17 further comprising the step of detecting growth of a non-target cell in the presence of the selected test compound from step (c), concurrently with or separately from step (d).

22. A method of identifying a candidate antimicrobial compound comprising the steps of:
  (a) determining $F_1/F_0$ ATP synthase activity in the presence and absence of a test compound;
  (b) selecting a test compound that produces a decrease in the $F_1/F_0$ ATP synthase activity;
  (c) detecting growth of microbial cells in the presence and absence of the test compound selected in step (b); and
  (d) selecting a test compound that inhibits growth of microbial cells.

* * * * *

UNITED STATES PATENT AND TRADEMARK OFFICE
CERTIFICATE OF CORRECTION

PATENT NO.    : 6,376,211 B1
DATED         : April 23, 2002
INVENTOR(S)   : Little et al.

It is certified that error appears in the above-identified patent and that said Letters Patent is hereby corrected as shown below:

<u>Columns 35-36,</u>
Line 29, Sequence 3, please delete "NH2 - (CH2) 7- CO" and insert in its place
-- $NH_2 - (CH_2)_7 - CO$ --.

<u>Column 38,</u>
Line 43, please delete "wherein the non-target cell is a mammnalian cell" and insert in its place -- wherein the non-target cell is a mammalian cell --.

Signed and Sealed this

Fifteenth Day of October, 2002

Attest:

Attesting Officer

JAMES E. ROGAN
Director of the United States Patent and Trademark Office